(12) United States Patent
Nowatschin et al.

(10) Patent No.: US 11,638,617 B2
(45) Date of Patent: May 2, 2023

(54) ROBOTIC MANIPULATOR FOR GUIDING AN ENDOSCOPE HAVING A PARALLEL LINKAGE

(71) Applicant: Brainlab Robotics GmbH, Munich (DE)

(72) Inventors: Stephan Nowatschin, Munich (DE); Maximilian Krinninger, Weßling-Oberpfaffenhofen (DE); Christian Kühnau, Munich (DE); Daniel Roppenecker, Munich (DE); Dominik Gierlach, Munich (DE); Johannes Agricola, Munich (DE); Johann Ulrich Wigger, Munich (DE)

(73) Assignee: Brainlab Robotics GmbH, Munich (DE)

( * ) Notice: Subject to any disclaimer, the term of this patent is extended or adjusted under 35 U.S.C. 154(b) by 678 days.

(21) Appl. No.: 16/616,436

(22) PCT Filed: May 14, 2018

(86) PCT No.: PCT/EP2018/062306
§ 371 (c)(1),
(2) Date: Nov. 22, 2019

(87) PCT Pub. No.: WO2018/215221
PCT Pub. Date: Nov. 29, 2018

(65) Prior Publication Data
US 2020/0138530 A1    May 7, 2020

(30) Foreign Application Priority Data

May 23, 2017    (DE) .................... 10 2017 111 296.0

(51) Int. Cl.
*A61B 34/30* (2016.01)
*A61B 90/50* (2016.01)
(Continued)

(52) U.S. Cl.
CPC .......... *A61B 34/30* (2016.02); *A61B 1/00128* (2013.01); *A61B 1/00133* (2013.01);
(Continued)

(58) Field of Classification Search
CPC ..... A61B 34/30; A61B 1/00149; A61B 90/50; A61B 1/00133
(Continued)

(56) References Cited

U.S. PATENT DOCUMENTS 11,472,043 B2 * 10/2022 Hongo .................... B25J 15/08
2020/0170488 A1 * 6/2020 Krinninger ............ A61B 34/70

FOREIGN PATENT DOCUMENTS

DE            20313514 U1   12/2003
DE   10 2014 016 823 A1    5/2016
(Continued)

OTHER PUBLICATIONS

Office Action issued in corresponding Korean Patent Application No. 10-2019-7037877 dated Sep. 13, 2022.

*Primary Examiner* — Todd M Epps
(74) *Attorney, Agent, or Firm* — Blank Rome LLP

(57) ABSTRACT

A surgical manipulator device for positioning a surgical instrument has a frame, a first mount, a second mount, a first suspension arm arrangement supported on the frame and connecting the frame to the first mount in an articulated manner, and a second suspension arm arrangement supported on the frame and connecting the frame to the second mount in an articulated manner. The first and the second suspension arm arrangements are each displaceable relative to the frame in first and second motion planes parallel to each other and spaced apart, so that the first mount is displaceable in the first motion plane and the second mount is displaceable in the second motion plane.

26 Claims, 18 Drawing Sheets

(51) Int. Cl.
*A61B 1/00* (2006.01)
*B25J 9/10* (2006.01)
*B25J 19/00* (2006.01)

(52) U.S. Cl.
CPC .......... *A61B 1/00149* (2013.01); *A61B 90/50* (2016.02); *B25J 9/107* (2013.01); *B25J 19/0004* (2013.01); *A61B 1/00016* (2013.01); *A61B 2034/301* (2016.02); *A61B 2090/506* (2016.02); *A61B 2090/508* (2016.02)

(58) Field of Classification Search
USPC ....................................................... 606/130
See application file for complete search history.

(56) References Cited

FOREIGN PATENT DOCUMENTS

| | | |
|---|---|---|
| DE | 10 2014 016 824 A1 | 5/2016 |
| DE | 10 2015 104 810 A1 | 9/2016 |
| DE | 10 2015 104 819 | 1/2018 |
| EP | 1 658 016 A1 | 5/2006 |
| EP | 3 130 305 A1 | 2/2017 |
| EP | 3130305 A1 * | 2/2017 ............ A61B 17/02 |
| KR | 10-2015-0023443 A | 3/2015 |
| WO | 01/34017 A2 | 5/2001 |
| WO | WO-0134017 A2 * | 5/2001 ............ A61B 34/70 |
| WO | 2005/030074 A1 | 4/2005 |
| WO | 2013/181526 A1 | 5/2013 |

* cited by examiner

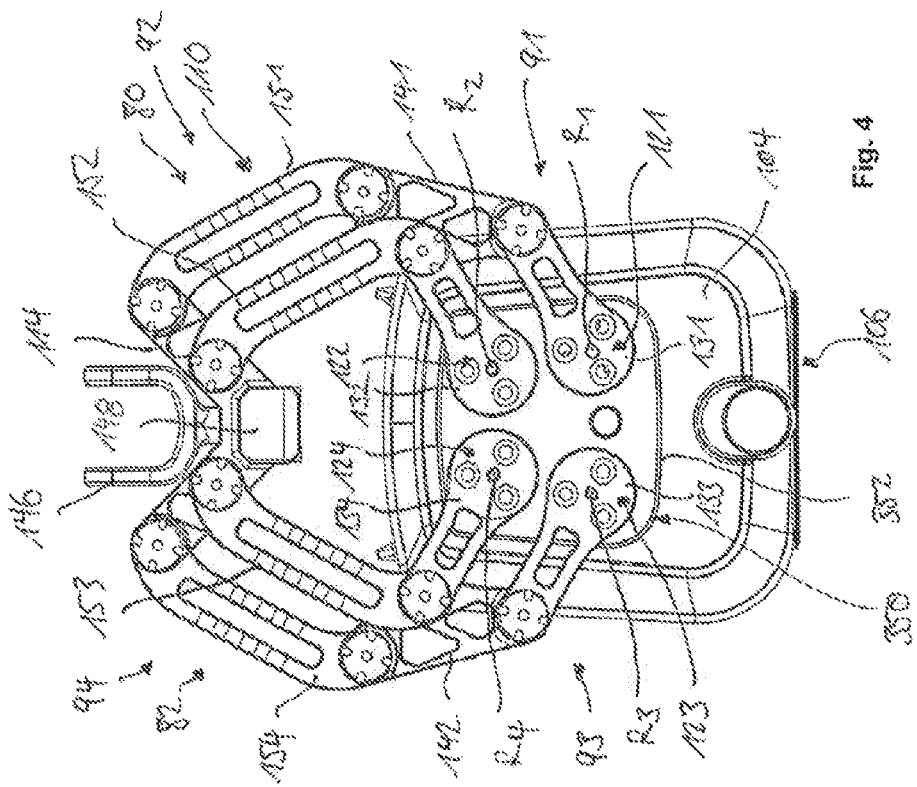

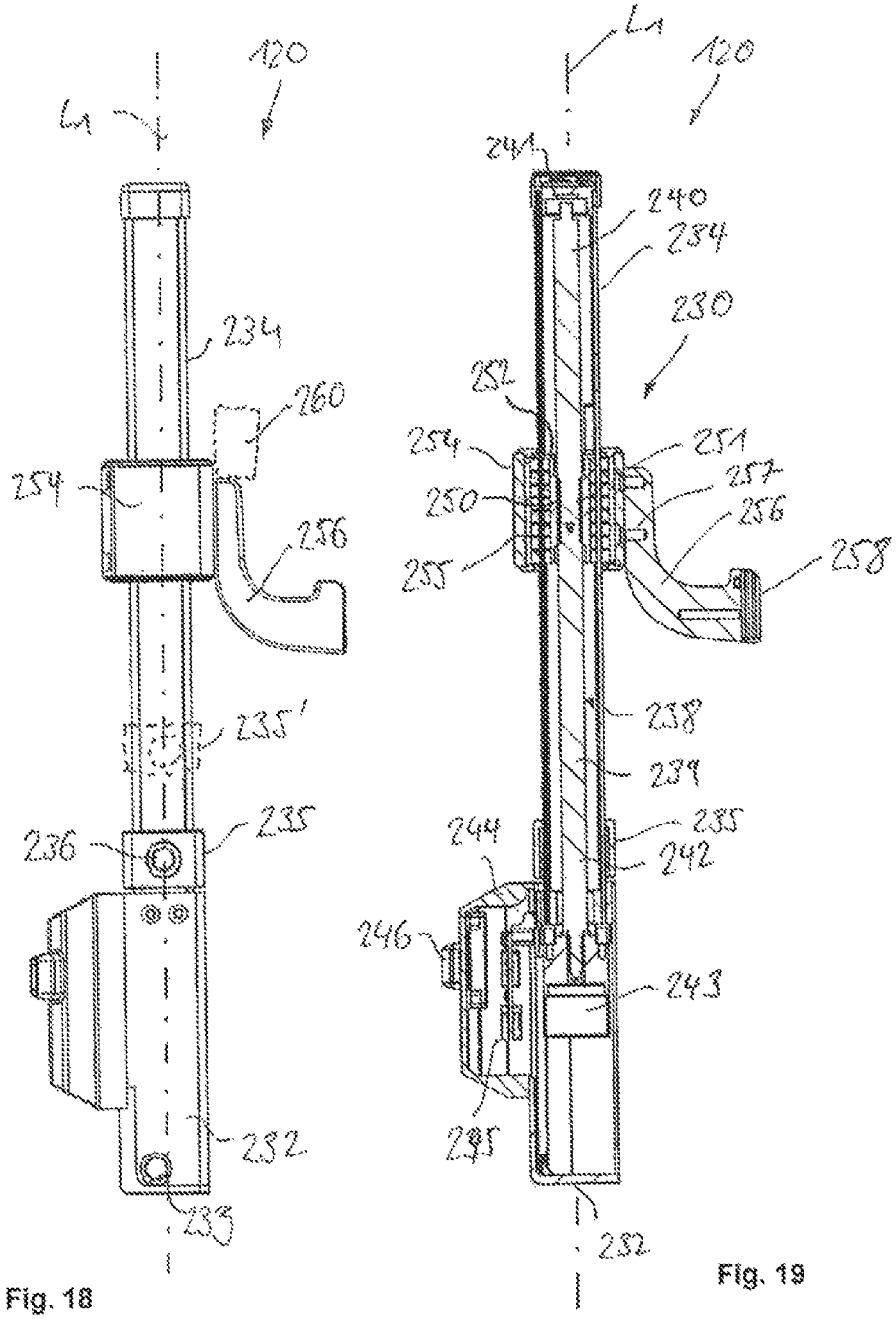

ROBOTIC MANIPULATOR FOR GUIDING AN ENDOSCOPE HAVING A PARALLEL LINKAGE

CROSS-REFERENCE TO RELATED APPLICATIONS

This application is a National Stage of International Patent App. No. PCT/EP2018/062306, filed on May 14, 2018, which claims priority to German Patent App. No. DE 10-2017-111-296.0, filed on May 23, 2017, the disclosures of which are incorporated by reference in their entirety.

FIELD OF THE INVENTION

The invention relates to a surgical manipulator device for positioning a surgical instrument, particularly an endoscope; to a method for positioning a surgical instrument, particularly an endoscope, by means of a surgical manipulator device; and to a coupling element for a surgical manipulator device.

BACKGROUND

Surgical manipulator devices are fundamentally known and are mounted particularly on a stand or mounting arm in surgery in order to hold particular surgical instruments during an operation or other examination.

Such a surgical manipulator device is known from EP 1 658 016 B1, for example. The device disclosed therein is provided for holding an endoscope and is fundamentally designed without a motor. The device comprises a frame having a suspension arm arrangement comprising at least two suspension arms and connecting the frame in an articulated manner to a first joint associated with the instrument, and having a second suspension arm arrangement comprising at least two suspension arms and connecting the frame in an articulated manner to a second joint associated with the first instrument, the suspension arms of the first suspension arm arrangement being pivotably supported relative to each other and relative to the frame about pivot axes, and the pivot axes running parallel to each other, and the two suspension arm arrangements being implemented so that the first joint is displaceable in a first motion plane and the second joint is displaceable in a second motion plane, characterized in that the first motion plane is displaceable relative to the second motion plane. Said arrangement is used in EP 1 658 016 for compensating for a changing distance of the first and second joints for different pivoting or displacing of the first and second suspension arm arrangements. This is necessary particularly because the instrument is directly connected to the joints. It is particularly disadvantageous for such a device that it is difficult to connect the frame to a stand, because the frame must also allow the displacement of the plane. The stability and rigidity of such a system is also not sufficient for some applications in surgery.

The surgical manipulator device of the present invention is particularly intended for mounting on a mounting arm, as described in DE 10 2014 016 823 A1, DE 10 2014 016 824 A1, DE 10 2015 104 810 A1, DE 10 2015 104 819 A1, and EP 3 130 305 A1. The disclosed contents thereof with respect to the mounting arm described therein is incorporated herein in their entirety.

SUMMARY OF THE INVENTION

One object of the present invention is therefore to provide a surgical manipulator device of the type indicated above, a method, and a coupling element for coupling to the mounting arm disclosed in DE 10 2014 016 823 A1, DE 10 2014 016 824 A1, DE 10 2015 104 810 A1, DE 10 2015 104 819 A1, and EP 3 130 305 A1, wherein the surgical manipulator provides high rigidity, small installation space, high precision for positioning, and a working and visual field as clear as possible for the surgeon.

The object is achieved for a surgical manipulator device of the type indicated above in that said device comprises: a frame, a first mount and a second mount for mounting an instrument socket for a surgical instrument, a first suspension arm arrangement supported on the frame and connecting the frame to the first mount in an articulated manner, and a second suspension arm arrangement connecting the frame to the second mount in an articulated manner, wherein the first and the second suspension arm arrangements are each displaceable relative to the frame in first and second motion planes parallel to each other and spaced apart, so that the first mount is displaceable in the first motion plane and the second mount is displaceable in the second motion plane, wherein the first suspension arm arrangement is coupled to the frame at four lever pivot points of the first suspension arm arrangement, and the second suspension arm arrangement is coupled to the frame at four lever pivot points of the second suspension arm arrangement.

According to the invention, a manipulator device is thus produced for displacing the first and second mounts in separate motion planes always disposed parallel to each other. Pivoting the planes relative to each other, as is proposed in the prior art, is not implemented by the present surgical manipulator device. A joint in the frame can thereby be eliminated and the frame can be more rigid overall. Each suspension arm arrangement is further coupled to the frame by means of four lever pivot points, whereby greater rigidity is achieved in turn. For purely positioning the first and second mount, two lever pivot points per suspension arm arrangement are fundamentally sufficient. The two further points provided according to the invention in each case then particularly serve for stabilizing.

The four first lever pivot points and the four second lever pivot points are preferably disposed in a V shape in each case. The suspension arm arrangements are thus prevented from assuming singularities. Due to the V-shaped arrangement of the four lever pivot points of each suspension arm arrangement, each position of the first and second mount is unique. Geometrically or statically indeterminate positions are avoided. The safety of the surgical manipulator device is thereby particularly substantially increased, because singularities cannot occur in the kinematics during an operation. An arrangement of the four first lever pivot points and the four second lever pivot points in a rectangle in each case is indeed preferred as part of the invention, but then other means should be provided for preventing singularities, such as a limit on freedom of motion.

The angle of the V preferably lies in a range from greater than 0° to 90° inclusive. It has been found that such an angle is particularly preferred. Furthermore, tendentially smaller angles, such as 45° or less, 30° or less, or 20° or less are preferable. The manipulator device is thereby more compact in design.

According to a first preferred embodiment, the second suspension arm arrangement is implemented substantially mirror-symmetrical to the first suspension arm arrangement. The first and second suspension arm arrangements are preferably intrinsically mirror symmetrical relative to a plane perpendicular to the planes of motion. The second suspension arm arrangement can be mirror-symmetrical to the first suspension arm arrangement in design, or identical to the first suspension arm arrangement and offset by a spacing. The number of parts is thereby reduced, and the number of identical parts can be increased. The manufacturing effort is thereby particularly reduced.

According to a further preferred embodiment, the four lever pivot points of the first suspension arm arrangement and the four lever pivot points of the second suspension arm arrangement are disposed on four common axes of rotation. That is, each joint of the first suspension arm arrangement has a common axis of rotation with a lever pivot point of the second suspension arm arrangement. For example, the first lever pivot point has a common axis of rotation with the fifth lever pivot point, the second lever pivot point has a common axis of rotation with the sixth lever pivot point, the third lever pivot point has a common axis of rotation with the seventh lever pivot point, and the fourth lever pivot point has a common axis of rotation with the eighth lever pivot point. The design is thereby further simplified and the suspension arm arrangements can be symmetrical in design. The freedom of motion and the working space of the surgical manipulator device is thereby particularly improved.

In a variant thereof, the four lever pivot points of the first suspension arm arrangement and the four lever pivot points of the second suspension arm arrangement are not disposed on four common axes of rotation. The axes of rotation are offset to each other in parallel. The initial orientation of the mounts relative to each other is thereby shifted, whereby an initial setting angle can be implemented. This has the advantage that an application-specific or patient-specific setting angle of the surgical instrument received by means of the mount can be implemented. The accessibility for instruments to an operating field can thereby be improved, for example, and/or the working space of the manipulator can be used more efficiently.

According to a further preferred embodiment, the first and second suspension arm arrangements are formed of a total of exactly three different suspension arm elements. Said three different elements are preferably levers, suspension arms, and bars. Said three different elements are described in more detail below. The inventors have determined that it is sufficient to use said three different elements in order to form the first and second suspension arm arrangements. The design is thereby simple and identical parts can be used. Costs are also thereby reduced.

The first suspension arm arrangement preferably comprises a first, a second, a third, and a fourth lever, each rotatably supported on first, second, third, and fourth lever pivot points of the first suspension arm arrangement on the frame. The first suspension arm arrangement further comprises a first suspension arm rotatably coupled to the first and second levers. Said arrangement further comprises a second suspension arm rotatably coupled to the third and fourth levers. The axes of rotation of the first and second levers preferably define a first leg of the V and the axes of rotation of the third and fourth levers preferably define a second leg of the V.

According to the invention, the first suspension arm arrangement comprises first and second bars rotatably coupled to the first suspension arm on one side and rotatably coupled to the first mount on the other side. The first suspension arm arrangement accordingly comprises third and fourth bars rotatably coupled to the second suspension arm on one side and rotatably coupled to the first mount on the other side. The first mount is thus coupled to the frame by means of the first suspension arm arrangement.

The first and second bars are preferably disposed parallel to each other. The third and fourth bars are also preferably disposed parallel to each other.

In a corresponding manner, the second suspension arm arrangement comprises a fifth, a sixth, a seventh, and an eighth lever, each rotatably mounted at fifth, sixth, seventh, and eighth lever pivot points of the second suspension arm arrangement on the frame. The second suspension arm arrangement comprises a third suspension arm rotatably coupled to the fifth and sixth levers and a fourth suspension arm rotatably coupled to the seventh and eighth levers. According to the invention, the second suspension arm arrangement comprises fifth and sixth bars rotatably coupled to the third suspension arm on one side and rotatably coupled to the second mount on the other side. In a corresponding manner, the second suspension arm arrangement comprises seventh and eighth bars rotatably coupled to the fourth suspension arm on one side and rotatably coupled to the second mount on the other side. In this manner, the second mount is coupled to the frame, as has already been described with respect to the first mount.

The fifth and sixth bars are preferably disposed parallel to each other. It is also preferable that the seventh and eighth bars are disposed parallel to each other.

According to a further preferred embodiment, the first suspension arm arrangement comprises a first, a second, a third, and a fourth parallelogram. The second suspension arm arrangement further preferably comprises a fifth, a sixth, a seventh, and an eighth parallelogram.

The first parallelogram is preferably formed by the first and second levers, the first suspension arm, and the frame. The second parallelogram is preferably formed by the first and second bars, the first suspension arm, and the first mount.

In a corresponding manner, the third parallelogram is preferably formed by the third and fourth levers, the second suspension arm, and the frame. The fourth parallelogram is preferably formed by the third and fourth bars, the second suspension arm, and the first mount. The third and fourth parallelograms are particularly provided for stabilizing and the first and second parallelograms for positioning the first mount. In the same manner, the fifth parallelogram is formed by the fifth and sixth levers, the third suspension arm, and the frame. The sixth Parallelogram is preferably formed by the fifth and sixth bars, the third suspension arm, and the second mount. The seventh parallelogram is preferably formed by the seventh and eighth levers, the fourth suspension arm, and the frame. The eighth Parallelogram is correspondingly preferably formed by the seventh and eighth bars, the fourth suspension arm, and the second mount. The sixth and eighth parallelogram also serve particularly for stabilizing, while the fifth and seventh parallelogram serve for positioning.

By connecting the parallelograms one after the other, the first mount is displaceable only in one plane, namely the first motion plane in the X and Y-directions. The second mount is accordingly displaceably only in the second motion plane, again in the X and Y-directions.

It is further preferable that the first and second parallelogram comprise a common joint. The third and fourth parallelogram further preferably comprise a common joint. The fifth and sixth and the seventh and eighth parallelogram also preferably each comprise a common joint. The design is thereby further simplified and the size of the surgical manipulator device is reduced. Because the parallelograms are each connected one after the other, the suspension arms each form an element of two parallelograms, so that it is possible to implement common joints.

According to a further preferred embodiment, the surgical manipulator device comprises a drive for the first and second suspension arm arrangements. It is thereby possible to drive the suspension arm arrangements in order to thus position the first and second mount in the first and second motion planes.

In a preferred refinement, the drive comprises a first and a second motor for the first suspension arm arrangement and a third and a fourth motor for the second suspension arm arrangement. The first, second, third, and fourth motors are preferably operable independently of each other. Said motors are preferably implemented as electric motors having a rotating output shaft. All four motors are preferably identical in design.

The first and second motors preferably drive the levers disposed distal to the first mount, and the third and fourth motors drive the levers disposed proximal to the second mount. That is, the first motor preferably drives the first lever, the second motor preferably drives the third lever, the third motor preferably drives the sixth lever, and the fourth motor preferably drives the eighth lever. If the levers altogether always share an axis of rotation in pairs, then an arrangement is achieved in which for each pair of levers sharing an axis of rotation, one lever is driven and the other lever is passive in each case. The size of the surgical manipulator device is thereby significantly reduced. The four motors of the drive can be disposed so that the axes of rotation thereof are each parallel to each other. It is not necessary for the individual motors to be disposed approximately coaxially and axially offset from one another, as no two motors share a common axis of rotation.

In a preferred variant or in addition, the surgical manipulator device comprises a braking device for actively braking the first and second suspension arm arrangements and a releasing unit for selectively releasing one or more degrees of freedom of the first and/or second suspension arm arrangement. The braking device comprises a first and a second brake for the first suspension arm arrangement and a third and a fourth brake for the second suspension arm arrangement. The first and second brakes preferably brake the levers disposed distal to the first mount, and the third and fourth brakes preferably brake the levers disposed proximal to the second mount. In this respect, the brakes are preferably disposed analogously to the motors described and can be inserted in the frame instead of the motors. A passive surgical manipulator device is thereby produced, the braking device thereof being particularly manually releasable by means of the releasing unit, in order to thus adjust the pose of the first and second suspension arm arrangements and the position of the first and second mount in the first and second motion planes.

The brakes of the braking device are preferably closed in the de-energized state. Said brakes are preferably implemented as electromagnetic brakes. By powering the brakes with electricity, said brakes are released and the pose of the first and second suspension arm arrangement can be adjusted.

The releasing unit preferably comprises a switch or the like and is coupled to the braking device. The braking device can have a braking control device controlling the brakes separately or jointly. The releasing unit is preferably implemented so that each brake can be released and locked separately and/or that all brakes can be released together. The releasing unit is preferably disposed apart from the frame, the braking device, and/or the first and second suspension arm arrangements, particularly on a surgical instrument being received, on a floor, or on an operating table, and is connected by means of a cable or wirelessly to the braking device for providing a releasing signal. The releasing unit can be implemented as a foot pedal, for example. In a further variant, the releasing unit comprises a switch and a base body and can be clipped to a surgical instrument received at the first and second mounts. It is thus possible for a user to actuate the releasing unit when picking up the surgical instrument, so that the brakes are released and the pose of the first and second suspension arm arrangements, and thus also the position of the surgical instrument, can be adjusted manually. Intuitive operation is thereby provided. In addition or alternatively, the releasing unit is wirelessly connected to the braking device or a braking control device of the braking device, for example by means of WIFI, Bluetooth, or a wireless transmitting system of a higher successive system. For example, the releasing unit comprises a software program for running on a handheld computer, for example a mobile telephone, a tablet PC, or the like. In a further variant, the releasing unit is implemented in the form of a remote control and provides the releasing signal to the releasing device by means of infrared radiation, said releasing device being equipped with a corresponding receiver for this purpose. It is also conceivable, however, that the releasing unit, in addition or alternatively, comprises a manually actuated switch disposed on the housing of the surgical manipulator device.

In a further preferred embodiment, the surgical manipulator device comprises an instrument receiving device coupled to the first and the second mount in an articulated manner. The instrument receiving device preferably comprises form-fit means set up for receiving a coupling element for the surgical instrument. According to the invention, the surgical instrument is not directly coupled to the first and second mounts, but rather an instrument receiving device is coupled to the first and the second mounts and the instrument can then be selectively connected to the instrument receiving device. It is conceivable that the surgical instrument is directly connected to the instrument receiving device, but it is preferable that the instrument is connected by means of a coupling element in turn connected to the instrument receiving device in a form-fit manner.

The instrument receiving device is preferably designed so as to allow a changing distance between the first and the second mount, due to the different positioning of the first and the second mounts in the first and the second motion planes. It is conceivable, for example, that the instrument receiving device is fixedly coupled to the first mount on one side, while a sliding guide and/or slip coupling is provided at the second mount, and the instrument receiving device is mounted on the second mount in said sliding guide or by means of the slip coupling. The sliding guide is preferably designed so that the instrument receiving device is displaceable relative to the second mount. Compensating for the changing distance between the first and the second mount is thereby possible without pivoting the first and the second motion planes relative to each other and without the first and second mounts having to depart the respective first and second motion planes. Tensions are thereby prevented. Furthermore, the torsional rigidity at the instrument receiving device is thereby increased, and the rigidity in the instrument receiving device is simultaneously reduced, which is advantageous for patient safety.

The coupling element is preferably formed from an insulating material in order to electrically insulate an instrument, if received in the coupling element, relative to the instrument receiving device. The safety of the surgical manipulator device is thereby substantially improved.

In a further preferred embodiment, the instrument receiving device comprises a linear drive for positioning the instrument at least partially perpendicular to the first and second motion planes. A further degree of freedom is thereby produced for the surgical manipulator device and the instrument can be displaced particularly perpendicular to the motion planes. This is advantageous particularly if an endoscope, a catheter, or a biopsy needle is received as the instrument, that is, instruments for displacing substantially along the longitudinal axis thereof during an examination.

In a preferred refinement, the linear drive comprises an elongated sleeve, a spindle drive disposed in the sleeve, and an output drive element supporting the form-fit means, wherein the spindle drive drives a magnetic driver disposed in the sleeve and the output drive element is supported externally and linearly displaceably on the sleeve and is coupled to the magnetic driver by means of magnetic force. In this manner, it is possible for the sleeve to be externally smooth and have no penetrations, grooves, or other recesses. Hygiene is thereby particularly improved. The magnetic driver in the interior of the sleeve is coupled to a spindle drive, and the spindle drive drives the magnetic driver and linearly displaces the same. A spindle drive has the advantage in general that high positioning accuracy can be achieved without introducing excessive electromagnetic fields, as would be the case for conventional electromagnetic linear drives, for example, A small electric motor is sufficient for driving the spindle and can be disposed at one end of the sleeve. Due to the purely magnetic coupling between the output drive element and the magnetic driver, it is also possible to remove the instrument and the output drive element from the instrument receiving device without fully disassembling the instrument receiving device.

According to a further preferred embodiment, the instrument receiving device comprises a rotary drive provided for rotating a received surgical instrument about an axis of rotation, wherein the axis of rotation preferably runs substantially parallel to a drive direction of the linear drive. A rotation of the surgical instrument about a further axis is thereby allowed. A surgical instrument is typically received at the instrument socket such that said instrument can be linearly driven along the longitudinal axis thereof, particularly with respect to an endoscope displaceable along the stick axis thereof. For angled optics, it is preferable to implement the rotary drive of the present embodiment in order to enlarge the field of vision.

According to a further preferred embodiment, the instrument receiving device comprises a force/moment sensor unit set up for capturing forces and moments acting on the instrument receiving device from a surgical instrument received at the instrument receiving device. The force/moment sensor unit is preferably coupled to the control unit of the surgical manipulator device and the control unit comprises software means set up for processing signals provided by the force/moment sensor unit and correspondingly controlling a drive of the surgical manipulator device and/or the linear drive of the instrument receiving device or another drive of the instrument receiving device. The force acting on the instrument receiving device from the instrument can represent a user's command. It is possible, for example, that a surgeon manually grasps the instrument received at the instrument receiving device and wishes to manually guide the instrument to a particular point. In this case, forces and moments act on the instrument receiving device from the instrument and are then captured by the force/moment sensor unit. Controlling in the present variant preferably comprises determining a motion and/or pose for the first and second suspension arm arrangements and/or the linear drive in order to compensate for forces and moments acting on the instrument receiving device, and controlling the drive and/or the linear drive corresponding to said motion or pose for performing or assuming said motion and/or pose.

For the case that the force on the received instrument is exerted by a patient instead of a user, for example because an operating error was made and the manipulator device has assumed a suboptimal pose or the patient has moved, said force is also reduced by said procedure and relief is provided. Safety is improved.

It is further preferable that the control unit receives signals from the force/moment sensor unit representing the weight of a mass received at the instrument socket. Said loading weight leads to a slight elastic deformation of the surgical manipulator device due to the finite rigidity of the system. In the present embodiment example, data representing the system rigidity is stored in the control unit of the surgical manipulator device. When determining the pose for achieving a desired specified position for the surgical instrument, the mass received at the instrument socket is preferably considered. In this case, the following steps are preferably performed for determining the pose: determining a deflection due to the received mass in the target pose of the first and second suspension arm arrangements; determining an adapted target pose based on the determined deflection; and displacing the first and second mounts by means of the first and second suspension arm arrangements to the adapted target pose for positioning the surgical instrument.

According to a further preferred embodiment, the surgical manipulator device comprises an electronic control unit having storage means and a processor for controlling a motion and positioning at least the first and second mounts. The electronic control unit is preferably also set up for controlling the linear drive of the instrument receiving device or another drive of the instrument receiving device.

It is further preferable that the surgical manipulator device comprises an electronic interface for receiving actuating signals from an upper-level control unit, particularly a surgical navigation system or a surgical mounting arm having the upper-level control unit. On one hand, it is conceivable that the surgical manipulator device receives actuating signals directly via the electronic interface for the drive of the first and second suspension arm arrangements and/or for the linear drive of the instrument receiving device or another drive of the instrument receiving device, and thus does not require intrinsic intelligence. On the other hand, it is also conceivable that the surgical manipulator device comprises the electronic control unit having storage means and a processor and is thus autonomously able to determine actuating signals for the drive and/or the linear drive of the instrument receiving device or another drive of the instrument receiving device, particularly based on inputs from a user or based on actuating signals received via the electronic interface. It is thus conceivable that a desired specified position of the surgical instrument is received via the electronic interface and the electronic control unit of the surgical manipulator device then determines corresponding actuating signals from said specified position for the drive and/or the linear drive of the instrument receiving device or another drive of the instrument receiving device, in order to control the drive and/or linear drive of the instrument receiving device or another drive of the instrument receiving device accordingly for causing the first and second suspension arm arrangements to displace and to position the first and second mounts and/or for controlling the linear drive of the instrument receiving device accordingly. The electronic interface can be implemented in one variant as a wired interface having physical contacts or as a wireless interface receiving the actuating signals wirelessly from the upper-level control unit. Wi-Fi interfaces, Bluetooth interfaces, infrared interfaces, or successor interfaces of a higher level of development are conceivable for this purpose. It is particularly preferred that the surgical manipulator device is coupled to a mounting arm as described above and the actuating signals are received from the mounting arm. The mounting arm can determine said actuating signals intrinsically in one embodiment, or the actuating signals are received by the mounting arm from an upper-level control system, such as a surgical navigation system, and provided to the surgical manipulator device.

It is further preferable that the surgical manipulator device comprises an integrated input system for receiving user entries. The integrated input system is preferably coupled to the control unit of the manipulator device, or the surgical manipulator device comprises a separate control unit for the integrated input system. In one variant, the integrated input system comprises a microphone for receiving spoken commands as user inputs. The control unit to which the integrated input system is preferably connected preferably comprises at least one processor and software means suitable for processing spoken commands in one variant and providing corresponding actuating signals to the drive of the first and second suspension arm arrangement, to the linear drive of the instrument receiving device, to another drive of the instrument receiving device, and/or to the braking device. It can be provided, for example, that when a "release" command is received, a corresponding release signal is provided to the braking device from the control unit connected to the integrated input system. In further variant, spoken commands of the user are simply recorded and saved in order to be able to output the same in an OP report. In this manner, it is possible to associate particular operation actions with particular user inputs, using settings of a surgical instrument.

It is further advantageous that the integrated input system comprises at least on camera observing the first and second suspension arm arrangements, the positions of the first and second mounts, a position of a surgical instrument received at the first and second mounts, and/or an OP field. Such a camera can, for example, detect which instruments are introduced into and removed from an operating area. In the present embodiment, the control unit preferably comprises software means implemented for detecting instruments introduced into and removed from the operating area using image recognition algorithms, for providing a time stamp for corresponding signals, and for saving and providing an OP record.

According to a further preferable embodiment, the surgical manipulator device comprises a housing having an indicator device for indicating one or more statuses of the surgical manipulator device. Such statuses can particularly comprise one or more of the following: displacing the first and/or second suspension arm arrangement, displacing a linear drive of an instrument socket, receiving signals, transmitting signals, reaching a specified position of the first and second mounts, reaching and/or exceeding a predefined working space of the surgical manipulator device, direction in which the first and/or second mounts are or are to be displaced, type of surgical instrument to be received, force acting on the surgical instrument when the surgical manipulator device is switched on, is in a standby mode, is waiting for a user input, and/or when receiving a software update, reaching or approaching a home position of the first and second suspension arm arrangements, the first and second suspension arm arrangements being present in or near an extreme position, the status of a coupling having a mounting arm, the status of a connection of a peripheral device to the electronic interface, the type of instrument received, particularly a 0° endoscope, 30° endoscope, 45° endoscope, exoscope, switchable angled optics, or specific devices from third-party companies, saving an assumed pose of the first and second suspension arm arrangement in an internal or external memory, the success of the saving, a graphic representation of the saved data (e.g., reproducing the saved pose), producing, using, and/or cutting a communications connection between the surgical manipulator device and an external input system, particularly a surgical navigation system, whether a translatory motion or rotary motion (pivoting and/or tilting motion) is performed by a received instrument, the distance between a received instrument and a target position, a preliminarily saved pose of the first and second suspension arm arrangements selected from an internal memory and for approaching and (e.g., reproducing the selected pose), a location of a pivot point of a received surgical instrument, a scaling factor for a motion of a received surgical instrument.

The indicator device is preferably set up for displaying a working space of the manipulator. To this end, the indicator device displays on a top side of the housing (relative to an initial setting of the manipulator) the working space for pivoting and tilting motions and for parallel displacement of the instrument in the plane. An upper and lower working space boundary of the instrument receiving device can also be shown by means of the indicator device using a corresponding pattern, a flashing frequency, a color, and/or an intensity of the illumination. A top indicator segment is preferably used for the upper working space boundary of the instrument receiving device, and a bottom indicator segment disposed at a bottom side of the housing (relative to the initial setting) lights up correspondingly for the lower working space boundary. The user can then very easily see whether and how much working space is available.

The indicator device is preferably set up for indicating how the working space of the surgical manipulator device is aligned relative to the original coordinate system thereof. For example, the working space must be rotated relative to a patient for the same alignment of the surgical manipulator device so that an alignment of a received surgical instrument to the patient is positioned sensibly and anatomically correctly. To this end, an angled instrument adapter having a corresponding angle correction can be used in some cases. Because the coordinate transformation is indicated, a user is always informed of the alignment.

The indicator device preferably comprises at least two, preferably at least four indicator segments, wherein each indicator segment is associated with a pair or one of the four lever pivot points of the first and/or second suspension arm arrangement. A first indicator segment is associated with the first and second lever pivot points of the first and second levers, for example, and a second indicator segment is associated with the third and fourth lever pivot points of the third and fourth levers. The indicator device can thereby indicate, for example, that the first and second levers are moving while the third and fourth levers are standing still. If the indicator device comprises four indicator segments, then the indicator device can also be used for indicating the motion of the fifth through eighth levers. The third segment can be used for indicating a motion of the fifth and sixth levers while the fourth indicator segment indicates a motion of the seventh and eighth levers. A user is thereby always informed whether the first and second suspension arm arrangements are moving and, if so, in which direction and which segment of the suspension arm arrangement is moving. The user can thus see whether the instrument is moving and in which direction the instrument is moving.

The indicator device preferably comprises one or more annular indicators. The indicator device preferably annularly surround the four lever pivot points. A simple optical association of the indicator device and particularly of individual indicator segments of the indicator device with lever pivot points is thereby possible, and intuitive understanding by the user is achieved. It is also conceivable that a separate annular indicator is provided for each lever pivot point coaxial to the joint axis.

It is further preferably that the indicator device is set up for indicating a motion of at least one part of the first and second suspension arm arrangements about a corresponding lever pivot point.

In a further consideration, the above object is achieved according to the invention by means of a method for positioning a surgical instrument, particularly an endoscope, by means of a surgical manipulator device, particularly according to any one of the preferred embodiments of a surgical manipulator device according to the first consideration of the invention described above, having the steps: determining a first vector for a first mount for mounting the surgical instrument and lying within a first motion plane; determining a second vector for a second mount for mounting the surgical instrument and lying within a second motion plane; displacing the first mount in correspondence with the first vector by means of a first suspension arm arrangement supported on the frame and connecting the frame to the first mount in an articulated manner; and displacing the second mount in correspondence with the second vector by means of a second suspension arm arrangement connecting the frame to the second mount in an articulated manner, wherein the first and second motion planes are always parallel to each other. It should be understood that the steps of the method can be performed simultaneously or one after the other, and that the sequence thereof need not necessarily correspond to that described. It should further be understood that the surgical manipulator device according to the first consideration of the invention and the method according to the second consideration of the invention have identical and similar refinements, as are particularly set forth in the dependent claims. In this respect, reference is made in full to the above description of the surgical manipulator device of the first consideration of the invention.

The method preferably also comprises the steps of determining a speed and sequence at which the first and second mounts are displaced in correspondence with the first and second vector. The method preferably further comprises the steps: determining a first rotation for the first mount; determining a second rotation for the second mount; rotating the first mount in correspondence with the first rotation by means of the first suspension arm arrangement supported on the frame; and rotating the second mount in correspondence with the second rotation by means of the second suspension arm arrangement; wherein the axes of rotation of the rotations are disposed perpendicular to the first and second motion planes. It should be understood that the axes of rotation of the first and second mounts are perpendicular to the motion planes. The axis of rotation of an instrument socket received at the mounts, however, need not be disposed perpendicular to the motion planes, rather said axis can also run at an angle. The displacing preferably corresponds to the first and second vectors and the rotating corresponds to the first and second rotations in an automated manner, particularly by means of an electrical drive provided in the surgical manipulator device.

It is further preferable that the method comprises the steps: receiving a first surgical instrument at the instrument socket; and capturing a pivot point of the first surgical instrument relative to an object by approaching the pivot point by means of the first and second mount and saving said position in a memory. The first surgical instrument can in this case also be a pivot point gage provided for determining the pivot point, or a probe instrument. A pivot point is generally understood to be a point of the surgical instrument substantially stationary relative to an object, for example the patient, or changing depending on the object, and about which the instrument must be rotated during an examination or operation. The endoscope for ENT surgery, for example, must be rotated about a particular pivot point, particularly lying approximately in the inlet region of the nasal atrium, substantially independently of the depth of penetration of the endoscope into the main nasal cavity.

Said pivot point is preferably saved in a memory. Specification are preferably also saved describing a change to the pivot point, for example depending on a depth of penetration of the surgical instrument into the body of the patient. The memory can be provided in the surgical manipulator device or separate therefrom. By saving the pivot point, said point can be used in subsequent operations or for determining motion paths, trajectories, and the like. Because the pivot point is approached by means of the instrument and by means of positioning the first and second mounts, the setting of the first and second suspension arm arrangements having a pivot point is known. Approaching a pivot point can be done manually, in that a surgeon guides the instrument to said location and the first and second suspension arm arrangements work passively in this case. Another possibility is approaching under manual control, in that a surgeon guides the instrument by means of a type of joystick or other operator control unit, for example, in order to guide the instrument to the pivot point.

According to a further preferred embodiment of the method, the determining of the first and second vectors is performed using the saved pivot point. The surgical manipulator can preferably be set in a pivot point mode and in a normal mode. In the pivot point mode, all motion paths and trajectories, particularly the first and second vectors and the sequential series of motions of the first and second suspension arm arrangement, are performed in correspondence with the first and second vectors considering the pivot point. That is, even for pivoting or other motions of the instrument, said instrument is always displaced about the pivot point. In normal mode, in contrast, the pivot point is not considered. The instrument can also be displaced outside of the pivot point, for example.

In this mode it is conceivable, for example, to displace the first and second suspension arm arrangement in relative motions to each other at a ratio of 1:1. That is, the instrument socket is not pivoted in this case, but only linearly displaced. The surgical manipulator is set to the pivot point mode and the normal mode preferably in response to a signal, for example initiated by a user by means of a switch on the surgical manipulator device or a switch disposed separately, for example a foot pedal. It is also conceivable that said signal is transmitted to the surgical manipulator device from an upper-level control unit, such as a surgical navigation system. This can be done by means of a wired connection or wirelessly.

A further preferred embodiment of the method comprises the steps: receiving a signal representing an approach request of the pivot point; and determining the first and second vector, such that a received surgical instrument is positioned at the pivot point. It is preferable that the saving of the pivot point takes place by means of a pivot point gage. Said pivot point gage is then removed from the socket after saving the pivot point, and another surgical instrument, in this case an endoscope or the like, is received at the instrument socket. The signal representing an approach request to the pivot point serves to then bring the tip of the endoscope to the pivot point again. Such an approach request signal can be initiated by a switch, for example, or by another external signal. The first and second vector are then determined such that the tip of the received surgical instrument is positioned at the pivot point. To this end, it can also be provided that an axial extent at least partially perpendicular to the first and second motion planes is considered. In this case, approaching the pivot point also preferably comprises actuating a linear drive of an instrument receiving device.

A further consideration of the method comprises the step: determining a transformation matrix between a base of the surgical manipulator device and the pivot point. In addition to the coordinates of the pivot point, a transformation matrix is preferably also determined and then comprises the current orientation of the surgical instrument in addition to the point coordinates, whereby a coordinate system can be represented at the pivot point. This is then particularly advantageous for graphic displays or further spatial transformations relative to the pivot point. The pivot point coordinates and transformation matrices are preferably defined relative to a base coordinate system defined by the surgical manipulator device or particularly preferably by a mounting device, such as a mounting arm or a stand, on which the surgical manipulator device is mounted. Such a base coordinate system is preferably relative to an operating table.

The coordinates of the pivot point and/or the transformation matrix are preferably provided at an interface, for example by means of a RESTful API interface.

According to a further embodiment of the method, the surgical instrument is preferably implemented as a probe instrument and the method comprises the steps: traveling to a first anatomical landmark of a patient by means of the probe instrument; saving first landmark data representing the pose of the first and second suspension arm arrangements and/or the position of the first and second mount; linking the first landmark data to first image data representing at least one prerecorded tomograph of the patient. Such prerecorded or preoperatively captured tomographs are typically produced by the patient for operations. Such tomographs can be captured by a CT device, for example. The method preferably further comprises the steps of traveling to a second anatomical landmark of a patient by means of the probe instrument; saving second landmark data representing the pose of the first and second suspension arm arrangements and/or the position of the first and second mounts at the second anatomical landmark of the patient; and linking the second landmark data to second image data representing at least one prerecorded tomograph of the patient. Third, fourth, and fifth or further anatomical landmarks can be processed in the same manner. In this manner, subsequent intra-operative collisions between the surgical instrument and surrounding tissues can be avoided and a planned motion path or trajectory can be implemented accordingly.

According to a third consideration of the invention, the object indicated above is achieved by a coupling element for a surgical manipulator device, particularly a surgical manipulator device according to any one of the preferred embodiments of a surgical manipulator device according to the first consideration of the invention described above, wherein the coupling element allows coupling a surgical instrument to an instrument receiving device, wherein the coupling element comprises a main body made of a flexible, electrically insulating material, wherein the main body comprises form-fit means for coupling to the instrument receiving device and a clamping segment for clampingly coupling to the surgical instrument.

A fourth consideration of the invention relates to an instrument receiving device for a surgical manipulator device, particularly according to any one of the preferred embodiments of a surgical manipulator device described above according to the first consideration of the invention and for receiving a surgical instrument, wherein the instrument receiving device comprises a linear drive for positioning the instrument, wherein the linear drive comprises an elongated sleeve, a spindle drive disposed in the sleeve, and an output drive element supporting the form-fit means, wherein the spindle drive drives a magnetic driver disposed in the sleeve and the output drive element is supported externally and linearly displaceably on the sleeve and is coupled to the magnetic driver by means of magnetic force.

BRIEF DESCRIPTION OF THE DRAWINGS

The invention is described in more detail below, using an embodiment example and referencing the attached figures. Shown are:

FIG. 4 a plan view of the surgical manipulator device according to FIG. 3, but without a surgical instrument;

FIG. 5 a bottom view of the surgical manipulator device according to FIG. 4;

FIG. 18 a side view of an instrument receiving device;

FIG. 19 a full section through the instrument receiving device from FIG. 18;

DETAILED DESCRIPTION

Figure 1:
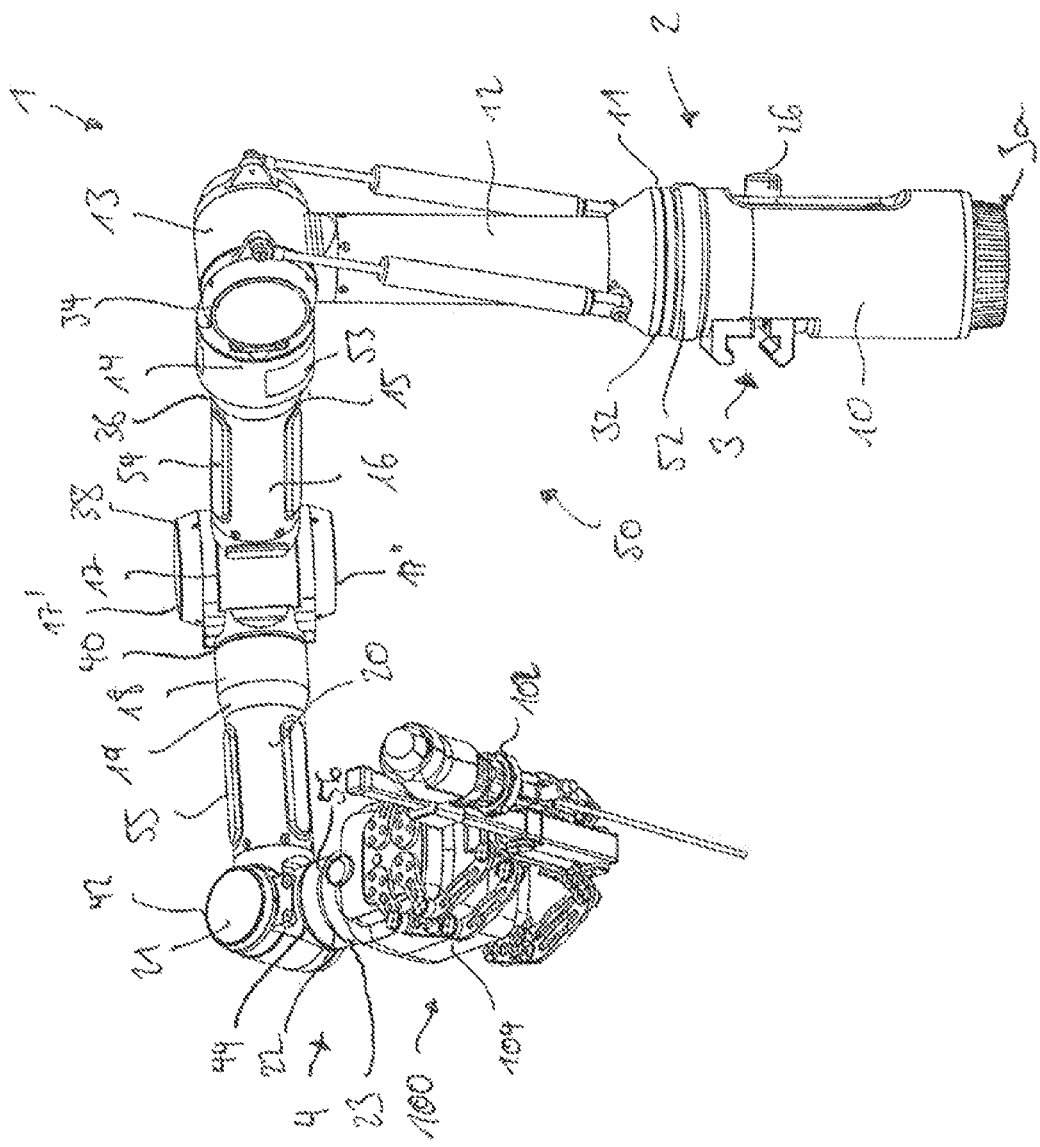
FIG. 1 a perspective view of a robotic mounting arm having a surgical manipulator device according to the invention.

According to FIG. 1, a mounting device 1 in the form of a robotic mounting arm is shown, on which a surgical manipulator device 100 is received. The mounting device comprises a proximal end 2 for attaching the mounting device 1 to a base (not shown). The base according to the present embodiment example can be implemented as a standard rail of an operating table (the operating table is not shown in FIG. 1). The mounting device 1 therefore comprises a clamping jaw 3 for manually clamping by means of a screw 3a. The mounting device 1 further comprises a distal end 4 for receiving an attached device, implemented here as a surgical manipulator device 100 according to the invention.

The mounting device according to FIG. 1 comprises seven arm segments 10, 12, 14, 16, 18, 20, 22, wherein the joints 11, 13, 15, 17, 19, 21, 23 are provided between the individual arm segments 10 through 22. The first arm segment 10 forms the proximal end 2 and comprises the clamping jaw 3. A power switch 26 is further provided on the arm segment 10 for switching on the entire mounting device, two connectors by means of which the mounting device is supplied with power and data, such as actuating signals and the like, and by means of which the data is transferred from the mounting device to external units such as operating room systems, and an emergency stop switch.

The joints 11, 15, 19, and 23 are implemented as rotary joints and the joints 13, 17, and 21 as pivot joints.

The mounting device 1 comprises an indicator unit 32, 34, 36, 38, 40, 42, 44 at each joint 11, 13, 15, 17, 19, 21, 23, each provided for indicating a status of the mounting device 1.

The indicator units 32, 34, 36, 38, 40, 42, 44 according to said embodiment example are substantially annular light sources, particularly implemented as LED rings. The central axis of each ring runs substantially coaxially to each axis of rotation of the joint 11, 13, 15, 17, 19, 21, 23. While one single LED ring is provided for each of the joints 11, 15, 19, 23, two LED rings are provided for each of the joints 13, 17, and 21. The two LED rings are provided at the front and rear joint segments 17', 17" (labeled with reference numerals as examples only in FIG. 1). Each display unit can always be detected in every position of the mounting device.

According to the present embodiment example, the mounting device further comprises an operator control device 50. The mounting arm can be placed in a desired pose by means of the operator control device 50, the operator control device 50 being set up for releasing the associated joint 11, 13, 15, 17, 19, 21, 23 upon contact between an operator and one of the seven arm segments 10, 12, 14, 16, 18, 20, 22. To this end, the operator control device 50 according to the present embodiment example comprises five contact segments 52, 53, 54, 55, 56, wherein each contact segment 52, 53, 54, 55, 56 is disposed on a different arm segment 11, 14, 16, 20, 22. The individual contact segments are implemented as touch-sensitive surfaces or buttons, so that one or more associated joints are released upon contact between a user and a corresponding contact segment.

The association of the individual joints 11, 13, 15, 17, 19, 21, 23 is regulated as follows according to the present embodiment example: upon contact between a user and the arm segment 10, that is, the contact segment 52, the joint 11 is released. A user can now influence one degree of freedom. When a user makes contact with the arm segment 14, the joint 15 is released; and upon contact with the contact means 54, the joint 13; upon contact with the contact means 55 the joints 19 and 17, and upon contact with the contact means 56 the joints 23 and 21. It is thereby preferably provided that the corresponding indicator units 32, 34, 36, 40, 42, 44 indicate said releasing, that is, particularly by lighting up the LED ring.

The precise construction of the mounting device and the function thereof are described in detail in DE 10 2014 016 823 A1, DE 10 2014 016 824 A1, DE 10 2015 104 810 A1, DE 10 2015 104 819 A1, and EP 3 130 305 A1. The disclosed contents of said publications are incorporated herein by reference in their entirety relating to the mounting arm 1.

The surgical manipulator device 100 in the present embodiment example holds an endoscope as the surgical instrument 102. The surgical manipulator device 100 comprises a housing 104 having an interface (cf. FIG. 23) by means of which the surgical manipulator device 100 is coupled to the distal end 4 of the mounting device 1. The interface 106 is described below in greater detail with respect to FIG. 23.

The surgical manipulator device 100 (also referred to below only as "manipulator device 100") further comprises a frame 108 (cf. FIGS. 16 and 17) defining a structure of the manipulator device 100. The frame is not visible in FIG. 2, as said frame is enclosed by the housing 104.

A first suspension arm arrangement 110 and a second suspension arm arrangement 112 are supported on the frame 108. The first suspension arm arrangement 110 is displaceable in a first motion plane B1 and the second suspension arm arrangement 112 is displaceable in a second motion plane B2 (cf. FIG. 3). The motion planes B1, B2 are parallel to each other and cannot be tilted relative to each other.

The first suspension arm arrangement 110 connects the frame 108 to a first mount 114 and the second suspension arm arrangement 112 connects the frame to a second mount 116. An instrument receiving device 120 is attached by means of the mounts 114, 116 in the present embodiment example (FIGS. 2 and 3) as is explained in greater detail with reference to FIGS. 18 and 19.

There can also be embodiments in which an instrument is directly connected to the first and second suspension arm arrangements 110, 112 without interconnecting an instrument receiving device 120. It is particularly also conceivable that a surgical instrument 102 is integrally formed with the first and second mounts 114, 116, and is particularly materially connected and cannot be non-destructively removed therefrom. For such a case, it can be preferable to provide a clip connection or the like between the first and second mounts 114, 116 and the corresponding first and second suspension arm arrangements 110, 112, in order to thus be able to change out the surgical instrument 102 of the surgical manipulator device 100.

The first suspension arm arrangement 110 is coupled to the frame 108 at four lever pivot points 121, 122, 123, 124 of the first suspension arm arrangement 110, and the second suspension arm arrangement 112 is coupled to the frame 108 at four lever pivot points 125, 126, 127, 128 of the second suspension arm arrangement (cf. FIG. 4, 5).

The first lever pivot point 121 comprises a first axis of rotation R1, the second lever pivot point 122 comprises a second axis of rotation R2, the third lever pivot point 123 comprises a third axis of rotation R3, and the fourth lever pivot point 124 comprises a fourth axis of rotation R4. The four lever pivot points 125, 126, 127, 128 of the second suspension arm arrangement 112 are labeled as the fifth lever pivot point 125, sixth lever pivot point 126, seventh lever pivot point 127, and eighth lever pivot point 128. In the present embodiment example (cf. FIGS. 3, 4, and 5), the four lever pivot points 121, 122, 123, 124 of the first suspension arm arrangement 110 comprise common axes of rotation R1, R2, R3, R4 with the four second lever pivot points 125, 126, 127, 128 of the second suspension arm arrangement 112. In this respect, the fifth lever pivot point 125 has the axis of rotation R1, the sixth lever pivot point 126 has the axis of rotation R2, the seventh lever pivot point 127 has the axis of rotation R3, and the eighth lever pivot point 128 has the axis of rotation R4.

Figure 3:
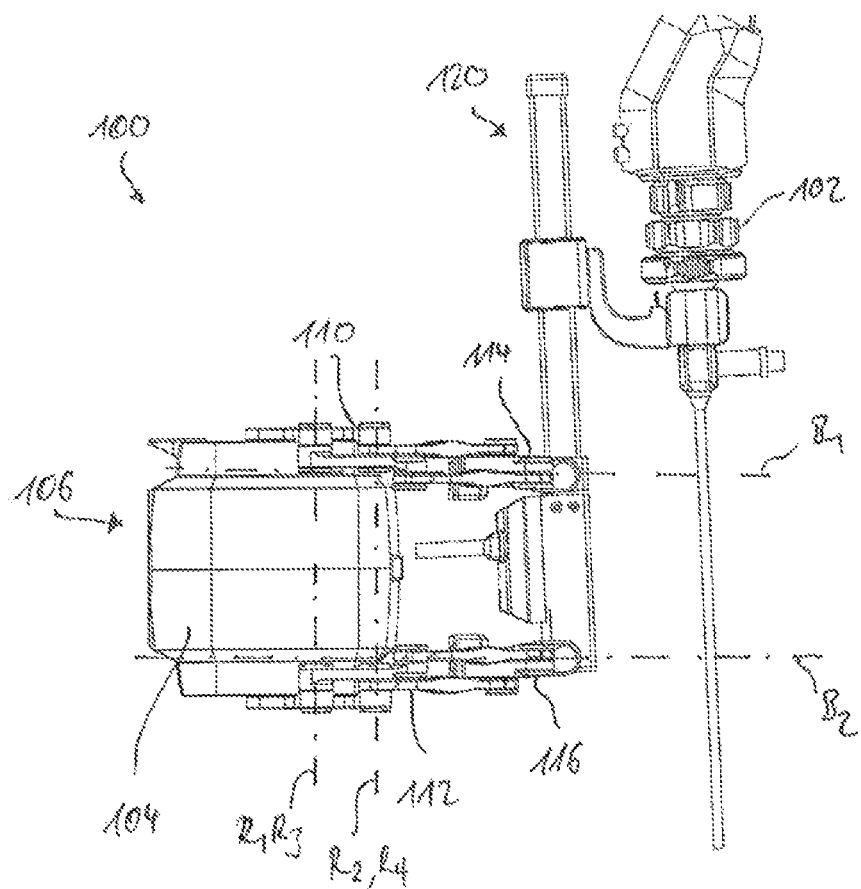
FIG. 3 a side view of the surgical manipulator device according to FIG. 2.

The first and second suspension arm arrangements 110, 112 are implemented identically, but mirror-symmetrically, in the present embodiment example, as can be seen particularly in FIGS. 3, 4, and 5; in the bottom view (FIG. 5) the second suspension arm arrangement 112 looks identical to the first suspension arm arrangement 110 of the plan view according to FIG. 4.

The first suspension arm arrangement 110 comprises first and second arm segments 80, 82, in turn identical and mirror-symmetrical to each other (cf. FIG. 4). The second suspension arm arrangement 112 comprises corresponding first and second arm segments 84, 86, in turn identical and mirror-symmetrical to each other.

Each of the arm segments 80, 82, 84, 86 comprises two parallelograms, namely a first parallelogram 91, a second parallelogram 92, a third parallelogram 93, and a fourth parallelogram 94. The second lever pivot arrangement 112 comprises a fifth parallelogram 95, a sixth parallelogram 96, a seventh parallelogram 97, and an eighth parallelogram 98.

The first suspension arm arrangement 110 comprises a first lever 131, a second lever 132, a third lever 133, and a fourth lever 134, the rotary axes thereof each being the axes of rotation R1, R2, R3, R4. In a corresponding manner, the second suspension arm arrangement 112 comprises a fifth lever 135, a sixth lever 136, a seventh lever 137, and an eighth lever 138, the rotary axes thereof also being the four axes of rotation R1, R2, R3, R4. It should be understood that there are also embodiment examples wherein the axes of rotation of the levers 135, 136, 137, 138 and thus also the axes of rotation of the fifth, sixth, seventh, and eighth lever pivot points 125, 126, 127, 128 are offset parallel to the axes of rotation R1, R2, R3, R4 and in this respect comprise four dedicated, separate axes of rotation. It is particularly conceivable that the lever pivot points 125, 126, 127, 128 are offset in the direction of the interface 106 in order to thus provide an initial setting angle for the surgical instrument 102 (cf. FIG. 3).

All levers 131 through 138 are connected to a suspension arm 141, 142, 143, 144 at the output side, that is, at the end opposite the lever pivot points 121 through 128. The first and second levers 131, 132 are connected to a first suspension arm 141 at the output side, the third and fourth levers 133, 134 are connected to a second suspension arm 142 at the output side, the fifth and sixth levers 135, 136 are connected to a third suspension arm 143 at the output side, and the seventh and eighth levers 137, 138 are connected to a fourth suspension arm 144 at the output side.

The first lever 131, the second lever 132, the first suspension arm 141, and the frame 108 together form the first parallelogram 91. The third lever 133, the fourth lever 134, the second suspension arm 142, and the frame 108 together form the third parallelogram 93. The fifth lever 135, the sixth lever 136, the third suspension arm 143, and the frame 108 together form the fifth parallelogram, and the seventh lever 137, the eighth lever 138, the fourth suspension arm 144, and the frame 108 together form the seventh parallelogram.

The first suspension arm arrangement 110 further comprises a first bar 151, a second bar 152, a third bar 153, and a fourth bar 154. The second suspension arm arrangement 112 comprises a fifth bar 155, a sixth bar 156, a seventh bar 157, and an eighth bar 158. The first and second bar 151, 52 connect the first suspension arm 141 to the first mount 114 in an articulated manner, and the third and fourth bar 153, 154 connect the second suspension arm 142 to the first mount 114 in an articulated manner. In a corresponding manner, the fifth bar 155 and the sixth bar 156 connect the third suspension arm 143 to the second mount 116 and the seventh and eighth bar 157, 158 connect the fourth suspension arm 144 to the second mount 116. The structure is explained again in greater detail with reference to FIG. 10.

A first cardan element 146 is further received at the first mount 114 and a second cardan element 147 is received at the second mount 116. The instrument receiving device 120 is held by means of the cardan elements 146, 147 as is described in detail below with reference to FIGS. 17 and 19. The first and second cardan elements 146, 147 are rotatably mounted in corresponding joint segments 148, 149 of the first and second mounts 114, 116.

FIG. 6 through 9 illustrate four different positions of the first mount 114 in a plan view, that is, in the plane B1. While the first mount 114 is shifted to an extreme left position in FIG. 6, the first mount 114 is shifted to an extreme right position in FIG. 7, to an extreme front position in FIG. 8, and to an extreme rear position in FIG. 9. Rotating about an axis perpendicular to the first motion plan B1 is not provided in FIG. 6 through 9 and cannot be implemented due to the parallel kinematics used here.

Figure 9:
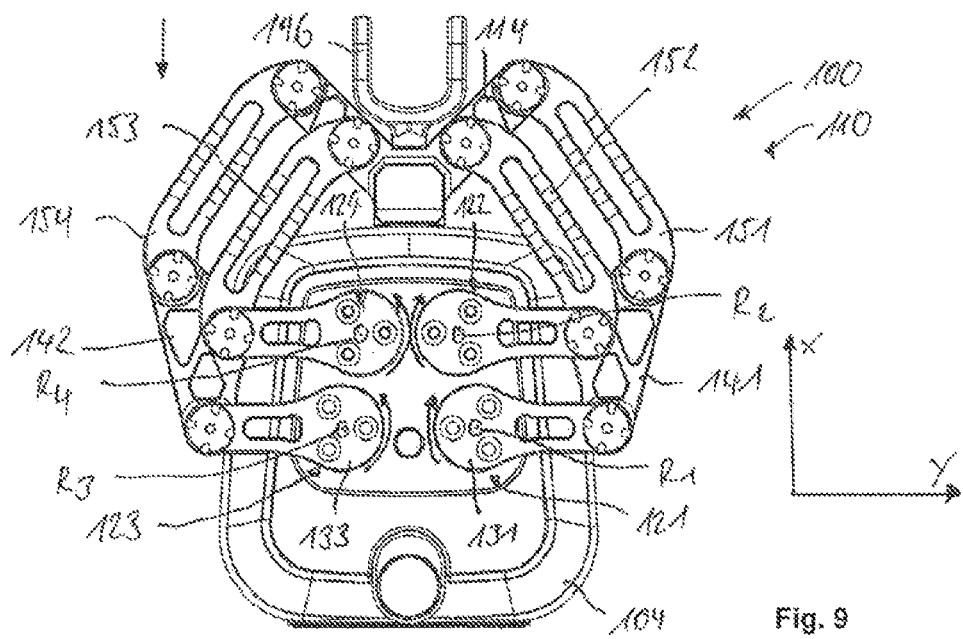
FIG. 9 the surgical manipulator device according to FIG. 4 in a fifth pose.

Shifting to the left side (FIG. 6, cf. arrow above the cardan element 146) is carried out in that the first and second levers 131, 132 are rotated to the left relative to the axes of rotation R1, R2, while the third and fourth levers 133, 134 are also rotated to the left relative to the axes of rotation R3, R4. Correspondingly rotating the levers 131, 132, 133, 134 in the opposite direction brings about a shifting of the first mount 114 to the right relative to FIG. 7, as illustrated by the arrow above the cardan element 146. If the levers 131, 132, 133, 134 are displaced in opposite directions in pairs, that is, the first and second levers 131, 132, are rotated in the opposite direction relative to the third and fourth levers 133, 134, then a shifting follows of the first mount 114 in an X-direction relative to the coordinate system shown within the first motion plane B1. This is also indicated by the arrow above the cardan element 146 (FIG. 8) and to the left of the cardan element 146 (FIG. 9).

As can be seen easily from FIG. 6 through 9, the suspension of the first mount 114 relative to the frame 108 is statically indeterminate. Just two levers, one suspension arm, and two bars would be sufficient for positioning the mount 114. It is conceivable, for example, to use only the levers 132, 134 and the bars 152, 153 for positioning the mount. It would also be possible to use only the levers 131,132, the suspension arm 141 and the bars 151, 152. The use of the present complex first and second suspension arm arrangements 110, 112 as shown, however, achieves a particularly high rigidity and thus a high positioning precision and repeatability.

Figure 10:
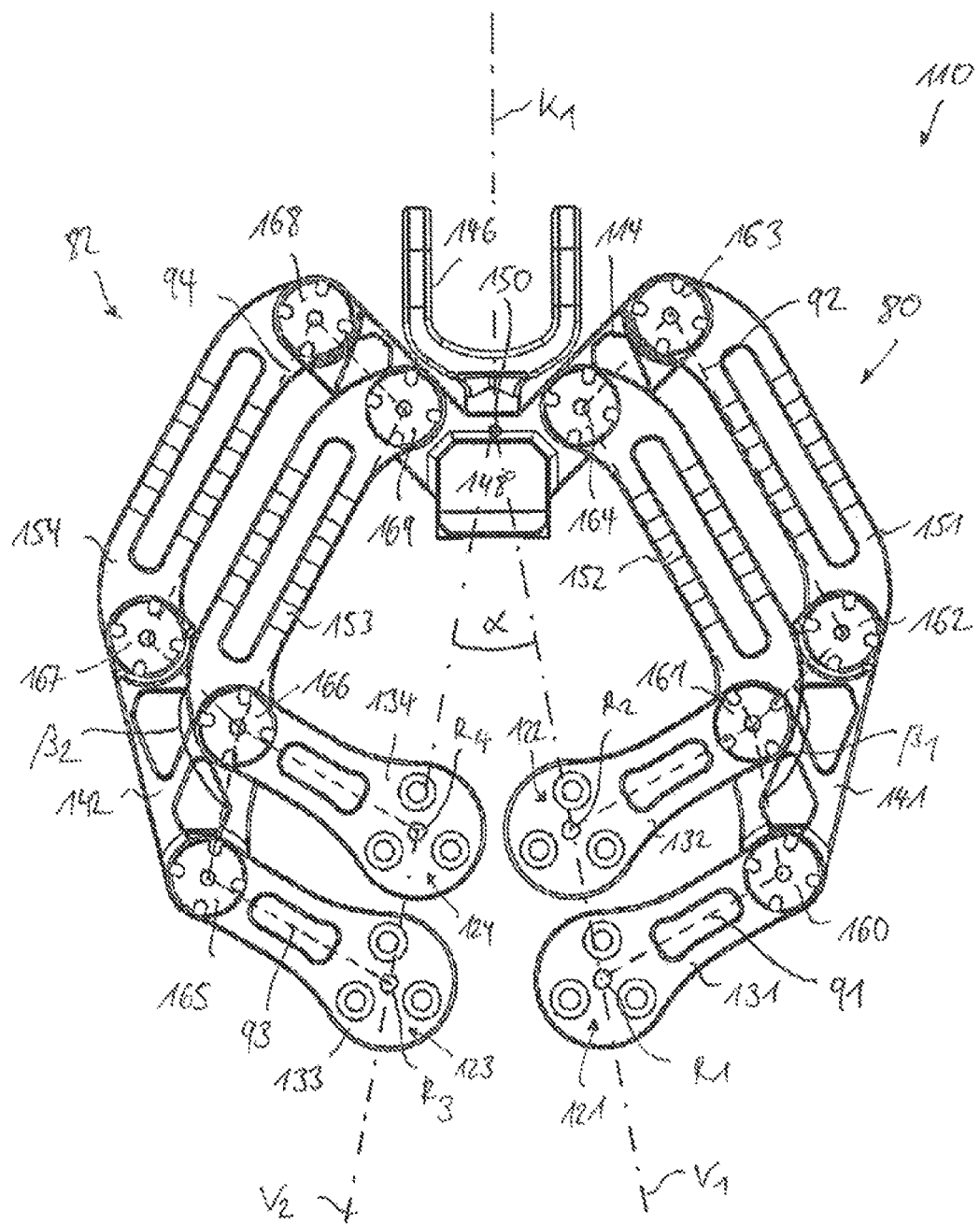
FIG. 10 a magnified view of the linkage of the surgical manipulator device.
Figure 11:
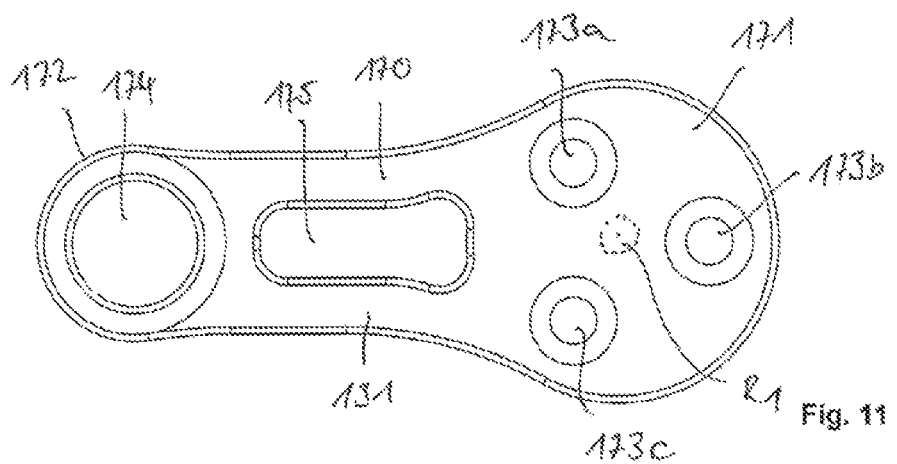
FIG. 11 a magnified view of a lever.
Figure 12:
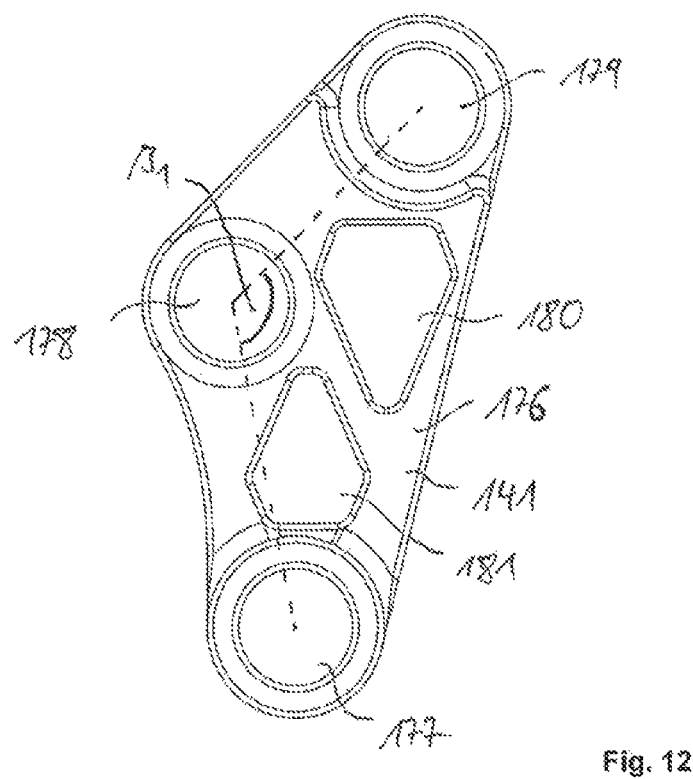
FIG. 12 a magnified view of a suspension arm.
Figure 13:
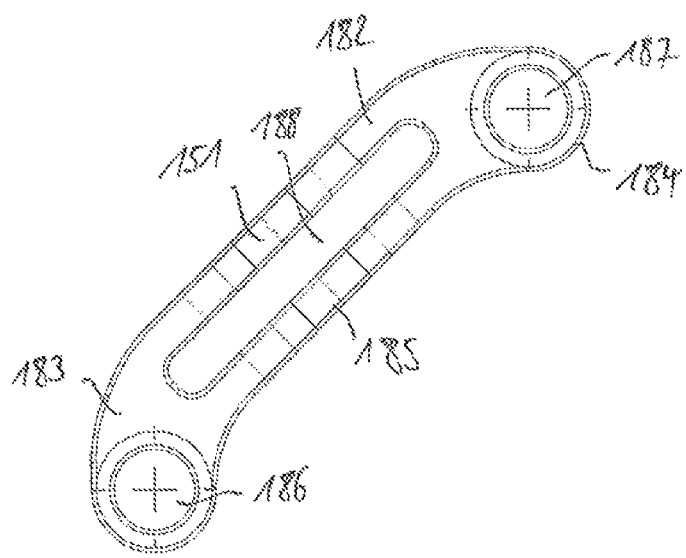
FIG. 13 a magnified view of a bar.
Figure 14:
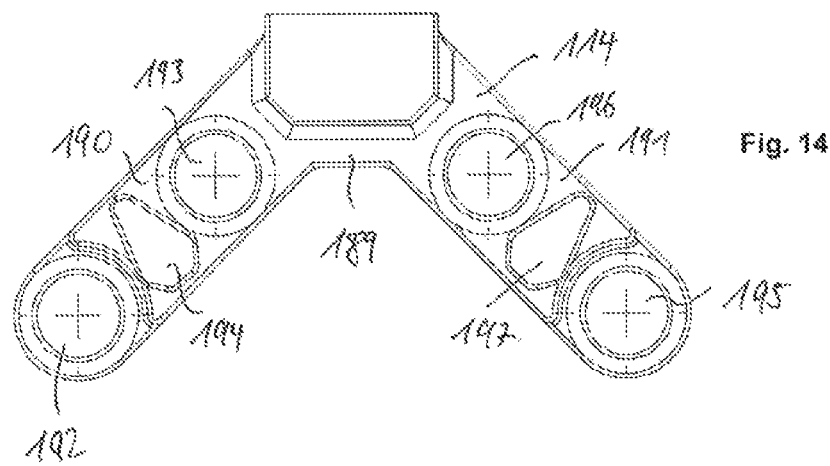
FIG. 14 a magnified view of a mount.
Figure 15:
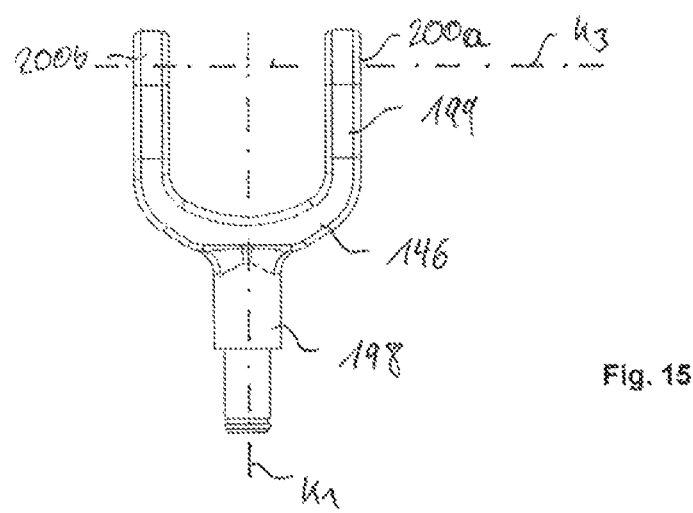
FIG. 15 a magnified view of a cardan element.

FIG. 10 shows the first suspension arm arrangement 110 including the first holder 114 and first cardan element 146 magnified again in order to better describe the geometry. The first, second, third, and fourth levers 131, 132, 133, 134, the first and second suspension arms 141, 142, and the first, second, third, and fourth bars 151, 152, 153, 154 are shown in turn. The first mount 114 and the first cardan element 146 are further shown. The first cardan element 146 is coupled to the socket 148 and is rotatable about an axis K1 lying within the first motion plane B1. Said element can also be shifted parallel to the same.

As can be seen particularly in FIG. 10, the levers 131, 132, 133, 134 are entirely identical in design. The suspension arms 141, 142, 143, 144 are also identical in design; the suspension arm 142 is simply reversed relative to the suspension arm 141, that is, disposed rotated 180 degrees about an axis parallel to the axis K1. The bars 151, 152, 153, 154 are also identical, wherein the bars 153, 154 are in turn rotated relative to the bars 151, 152. The same suspension arms are also used for the second suspension arm arrangement 112. This is not shown, as the illustration would be identical to illustration 10 and only the reference numerals would be changed.

The first, second, third, and fourth parallelograms 91, 92, 93, 94 are further drawn in FIG. 10 by means of dashed lines.

A further detail shown in FIG. 10 is the joints 160 through 169 of the first suspension arm arrangement 110. The first lever 131 is connected in an articulated manner to the first mount 141 by means of a first joint 160, and the second lever 132 is connected in an articulated manner to the first mount by means of a second joint 161. The first bar 151 is connected in an articulated manner to the first suspension arm 141 by means of a third joint 162, and the to the first mount 141 by means of a fourth joint 163. The second bar 152 is connected in an articulated manner to the first mount 114 by means of a fifth joint and to the first suspension arm 141 on the other side, also by means of the second joint 161. The second joint 161 thus forms a common joint for the first and second parallelograms 91, 92. An angle β1 is provided between the first and second parallelograms 91, 92 and defined by the geometry of the first suspension arm 141, more precisely by the arrangement of the first, second, and third joints 160, 161, 162. It has been found that the angle β1 should lie within a range from 90° to <180° in order to allow the use of identical parts, that is, of identical bars 151 through 158, identical levers 131 through 138, and identical suspension arms 141 through 144.

For the second arm segment 82, the same applies as for the first arm segment 80. The third lever 133 is connected in an articulated manner to the second suspension arm 142 by means of a sixth joint, and the fourth lever 134 is connected in an articulated manner to the second suspension arm 142 by means of a seventh joint 166. The third bar 153, in turn, is connected in an articulated manner to the second suspension arm 142 by means of the seventh joint 167, and to the first mount 114 by means of a tenth joint 169 on the other side. The fourth bar 154 is connected in an articulated manner to the second suspension arm 142 by means of an eighth joint 167, and the fourth bar 154 is connected in an articulated manner to the first mount 114 by means of a ninth joint 168. The third and fourth parallelograms 93, 94 in turn form an angle β2 corresponding to the angle β1.

As can be further seen in FIG. 10, the lever pivot points 121, 122, 123, 124 are disposed in a V shape, and the axes of rotation R1, R2, R3, R4 are disposed in a V shape. The V shape is described by the two axes V1, V2 drawn in FIG. 10 as dashed lines. The angle α of the V lies in a range from >0° to 90°. The vertex 150 of the V, that is, the intersection of the axes V1, V2 lies in the first mount 114 here, and thus in the working space of the linkage. The V-shaped arrangement of the lever pivot points 121, 122, 123, 124, 125, 126, 127, 128 avoids singularities of the first and second suspension arm arrangements 110, 112.

FIG. 11 through 15 show the three elements (lever, suspension arm, and bar) of the suspension arm arrangements 110, 112 separately again and the mount and the Cardan element. Only the first of said elements are shown as examples, wherein the further elements are always identical in design.

The suspension arm 131 (FIG. 11) is made as a single piece and comprises a round body 170 having a drive segment 171 and an output drive segment 172. The drive segment 171 of the lever 131 is connected in an articulated manner to the frame and comprises three pass-through openings 173a, 173b, 173c for mounting, serving for receiving mounting screws. The three pass-through openings 173a, 173b, 173c are disposed in a circle and equidistant from the axis of rotation R1. A further pass-through opening 174 is implemented at the output drive segment 172 and serves for receiving the first joint 160. An opening 175 is provided in the middle segment of the body 170 for weight reduction purposes. The levers 132 through 138 are identical in design.

The suspension arm 141 (cf. FIG. 12) comprises a base body 176. A first pass-through opening 177 for the first joint 160, a second pass-through opening 178 for the second joint 161, and a third pass-through opening 179 for the third joint 162 are implemented in the base body 176. Said pass-through openings 177, 178, 179 are each designed for receiving corresponding joint bushings of the joints 160, 161, 162. The pass-through openings 177, 178, 179 are disposed so as to enclose the angle β1, that is, the angle β1 between the first and second parallelograms 91, 92. The angle β1 can be modified by a corresponding design of the first mount 141. The angle β1 also influences the geometry of the first mount 114, for example, because the first mount 114 forms part of the second parallelogram 92.

The body 176 further comprises two further pass-through openings 180, 181 also provided for weight purposes. The second, third, and fourth suspension arms 142, 143, 144 are in turn identical in design to the suspension arm 141.

The first bar 151 (cf. FIG. 13) comprises a base body 182. Two end segments 183, 184 extend at slight angles, each at about a 45 degree angle from the middle part 185 of the bar 151. Pass-through openings 186, 187 are made in the end segments 183, 184 for receiving the third joint 162 and the fourth joint 163. The pass-through openings 186, 187 are in turn formed so that bearing bushings can be received. An elongated pass-through opening 188 is made in the middle part 185, in turn substantially for weight purposes. The pass-through opening 188, however, also provides an improved field of vision for the surgeon or user when using the surgical manipulator device 100 according to the invention. The other bars 152 through 158 are identical in design to the first bar 151. The bar 151 is altogether implemented as a single piece and is milled from aluminum, for example.

The first mount 114 (cf. FIG. 14) comprises a base body 189 and is altogether produced as a single piece. The mount 114 comprises a first and a second arm 190, 191, wherein the first arm 190 is provided for the first and second bars 151, 152 and the second arm 191 for the third and fourth bars 153, 154. A first and second pass-through opening 192, 193 are made in the first arm 190 for this purpose, serving for receiving joint bushings and forming a socket for the fourth and fifth joints 163, 164. A third pass-through opening 194 is made between the first and second pass-through openings 192, 193 for weight reduction purposes. In a corresponding manner, the second arm 191 comprises a first and second through hole 195, 196 implemented for receiving joint bushings and serving for receiving the ninth and tenth joints 168, 169. A third pass-through opening 197 is provided between said holes and is made for weight reduction purposes. The second mount 116 is identical in design.

The first Cardan element 146 (cf. FIG. 15) is formed as a single piece, for example of aluminum. Said element comprises a shaft 198 for receiving in the socket 148. A fork 199 extends from the shaft 198 and serves for receiving the instrument receiving device 120. The fork 199 comprises penetrations 200*a*, 200*b* (not visible in FIG. 15) to this end along an axis K3 perpendicular to the axis K1. In this manner, the instrument receiving device 120 can be fully rotatably received at the first and second mounts 114, 116.

Figure 16:
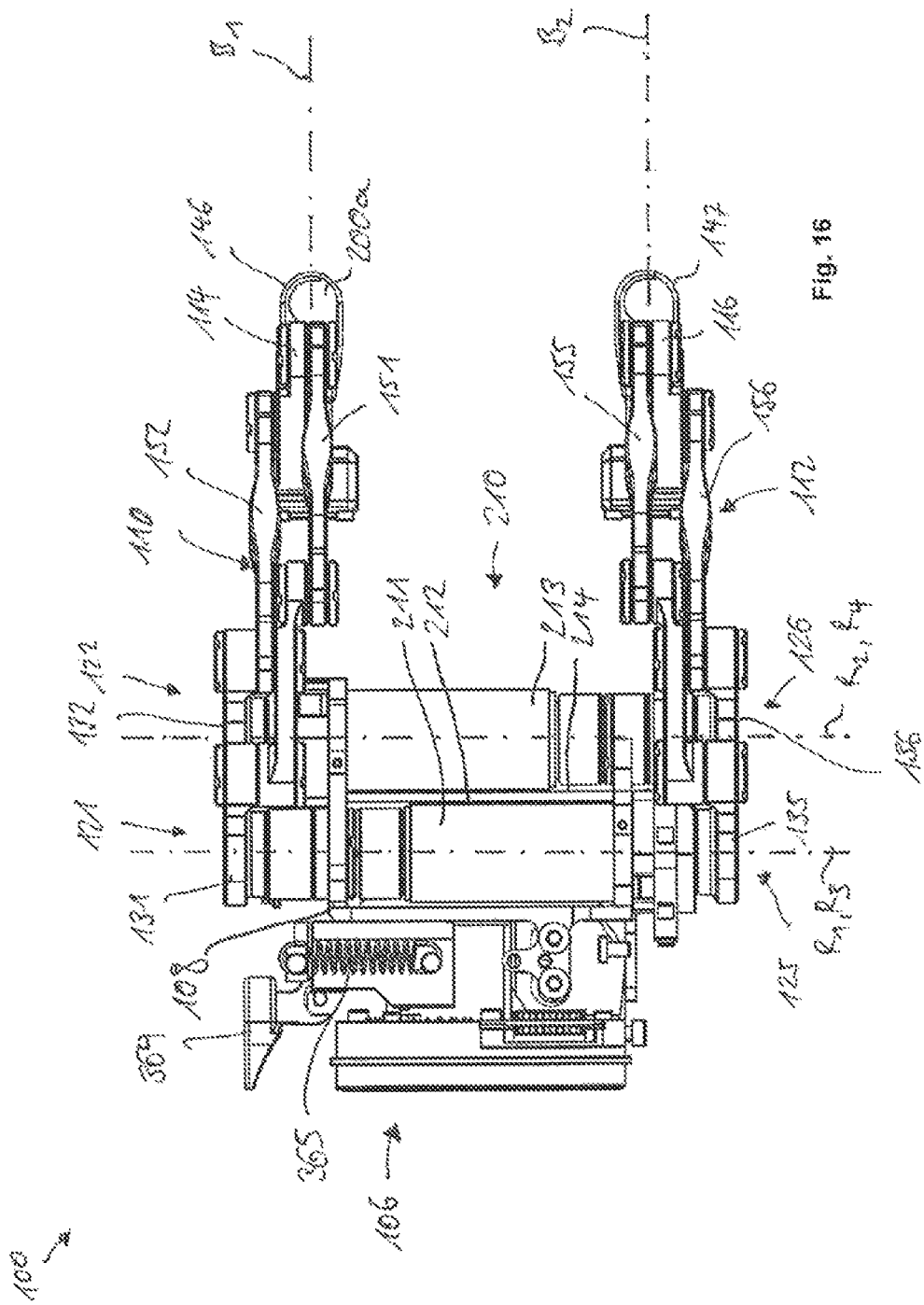
FIG. 16 a side view of the surgical manipulator device without the housing and having a drive.

In one embodiment of the surgical manipulator device 100, said device comprises a drive 210 (FIG. 16). The housing 104 and boards disposed within the housing 104 are left out of FIG. 16 in order to make the drive 210 visible. The drive 210 in the present embodiment example comprises four motors 211, 212, 213, 214. Of said four motors 211, 212, 213, 214, the motors 212, 214 are covered in FIG. 16 by the motors 211, 213. While the first and second motors 211, 212 are provided for the first suspension arm arrangement 110, the third and fourth motors 213, 214 are provided for the second suspension arm arrangement 112. The motors 211, 212, 213, 214 are disposed having axes of rotation on the axes of rotation R1, R2, R3, R4. That is, the first motor 211 is coupled to the first lever 131, and the second motor 212 is coupled to the third lever 133. In a corresponding manner, the third motor 213 is coupled to the sixth lever 136 and the fourth motor 214 is coupled to the eighth lever 138. The first and second motors 211, 212 thus drive the levers 131, 133 disposed distal to the first mount 114, while the third and fourth motors 213, 214 drive the levers 136, 138 disposed proximal to the second mount 116. A gearbox for changing the torque and rotary speed is preferably provided between the motors 211, 212, 213, 214 and the corresponding levers 131, 133, 136, 138. The motors 211, 212, 213, 214 are implemented here as brushless DC motors.

Due to the special double parallel linkage of the first and second suspension arm arrangements 110, 112, it is sufficient that only two levers of each of the four-lever suspension arm arrangement 110, 112 are driven. The motors 211, 212, 213, 214 can thereby also be placed such that said motors are adjacent to each other, parallel adjacent to each other, and not axially offset on a common axis of rotation. The size of the surgical manipulator device 100 can thereby be significantly reduced, as is particularly evident in FIG. 16.

A control unit is provided for controlling the motors 211, 212, 213, 214 and receives signals via the interface 106. This is described in detail further below.

Figure 17:
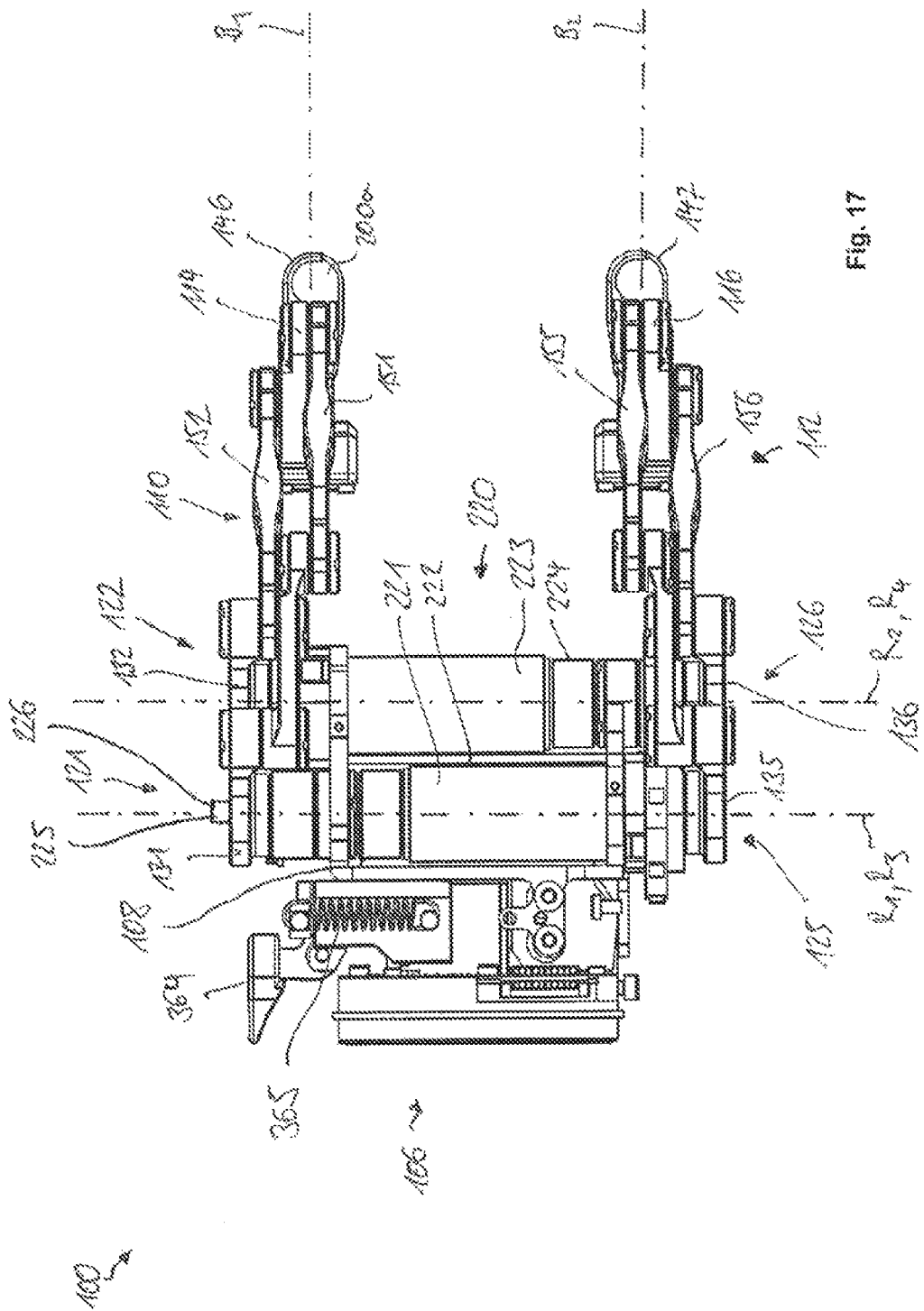
FIG. 17 a side view of the surgical manipulator device without the housing and having brakes for the linkage.

FIG. 17 shows a second embodiment of the manipulator device 100 comprising no drive 210 but rather a braking device 220 for actively braking the first and second suspension arm arrangements 110, 112. The braking device 220 comprises four brakes 221, 222, 223, 224 mounted to the frame 108 in a similar matter to the motors 211, 212, 213, 214. The first brake 221 in turn covers the second brake 222, and the third brake 223 covers the fourth brake 224. The brakes 221, 222, 223, 224 are each disposed coaxial to the axes of rotation R1, R2, R3, R4. The first brake 221 is coupled to the first brake 131, and the second brake 22 correspondingly to the third brake 133. In a corresponding manner, the third brake 223 is coupled to the sixth lever 136 and the fourth brake 224 is coupled to the eighth lever 138. The brakes 221 through 224 are implemented as electromagnetic brakes and closed in the de-energized state.

The surgical manipulator device 100 comprises a releasing unit 225 for releasing the braking device. One or more degrees of freedom of the first and/or second suspension arm arrangement 110, 112 can be released by means of the releasing unit 225. In the present embodiment example (FIG. 17), the releasing unit 225 is implemented as a pushbutton 226 and is also disposed on the frame 108, such that said pushbutton is accessible from outside the housing 204 (cf. particularly FIG. 23). By pressing said pushbutton 226, all brakes 221, 222, 223, 224 are released and the first and second suspension arm arrangements 110, 112 and thus also the positions of the first and second mounts 114, 116 can be adjusted. In this manner, a passive surgical manipulator device is formed and can be place in a desired pose by a user in a simple manner and locked in place, namely by pressing the pushbutton 226 and manually adjusting. The pushbutton 226 must merely be released for locking. The brakes 221, 222, 223, 224 are then de-energized and clamp closed. The pose of the first and second suspension arm arrangements 110, 112 is locked.

As mentioned above, an instrument receiving device 120 can be received at the first and second mounts 114, 116, optionally intermediately connected to the first and second Cardan elements 146, 147. The instrument receiving device is also independently claimed according to the invention, as shown in FIGS. 18 and 19. The instrument receiving device 120 can also be used with different manipulators and not solely with the surgical manipulator device described in FIGS. 1 through 17.

The instrument receiving device 120 shown in the embodiment example according to FIGS. 18 and 19 is not only usable as a rigid stand (although said use is preferable according to the invention) but also comprises a linear drive 230. In detail, the instrument receiving device 120 initially comprises a foot housing 232, the outside of which has a recess 233 (a further recess is disposed on the opposite side of the foot housing 232 with respect to FIG. 18), by means of which the foot housing 232 can be received in a Cardan element 146, 147 in a form-fit manner but pivotably about the axis K3, particularly the bottom Cardan element 147 (cf. FIGS. 2 and 15). A sleeve 234 fixedly connected to the foot housing 232 extends along a longitudinal axis L1 upward with respect to FIG. 18. The sleeve 234 has a substantially rectangular or square base shape (cf. FIG. 1) and is preferably made of a plastic or a non-magnetic material.

Figure 6:
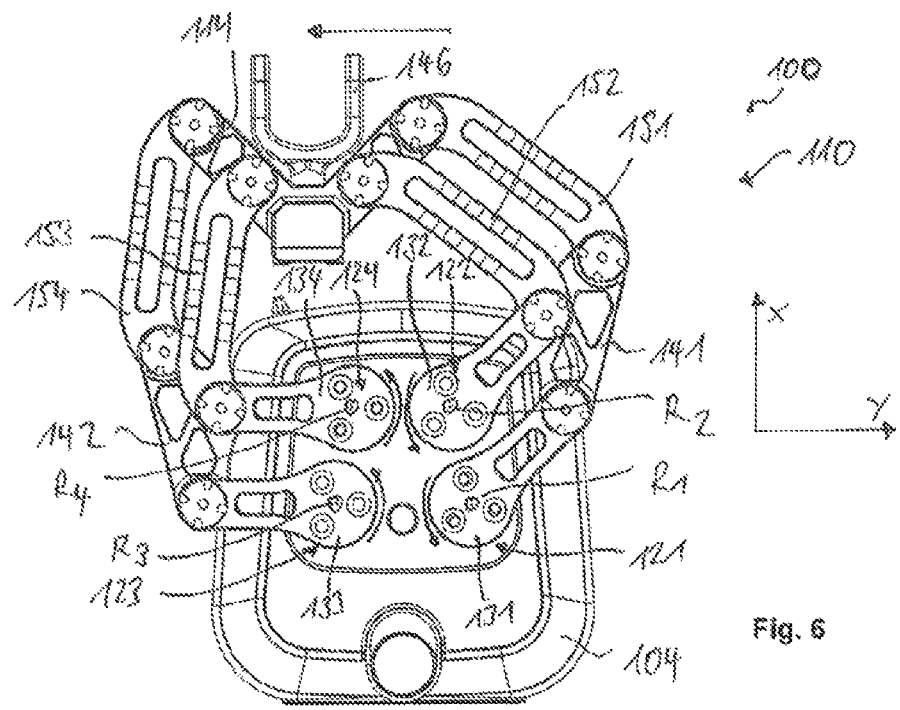
FIG. 6 the surgical manipulator device according to FIG. 4 in a second pose.
Figure 7:
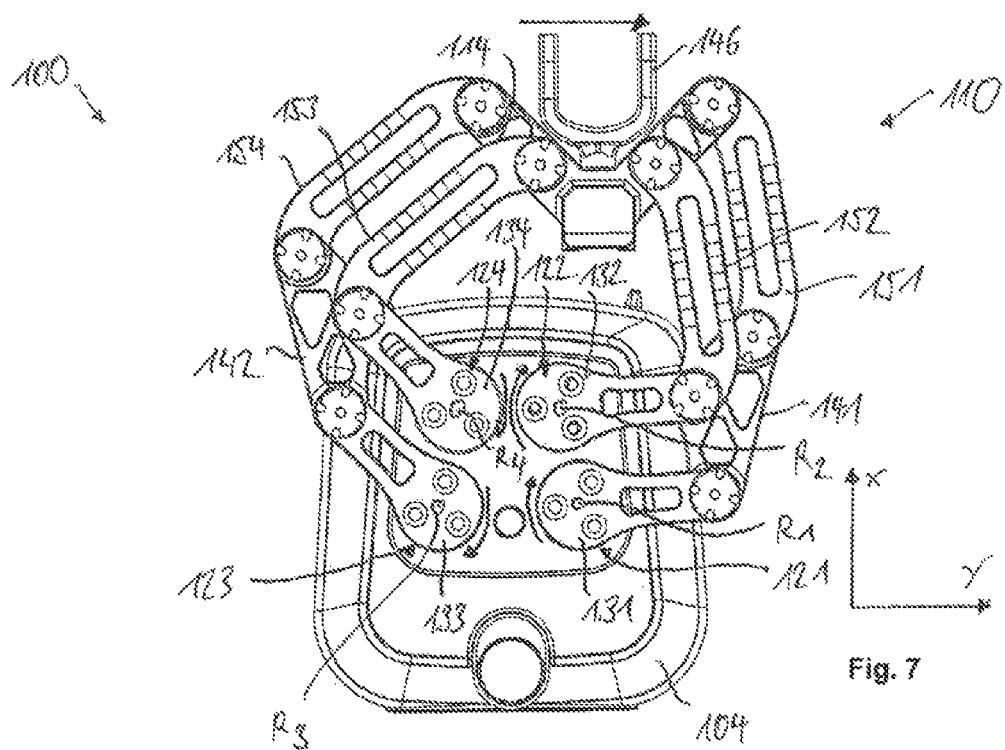
FIG. 7 the surgical manipulator device according to FIG. 4 in a third pose.
Figure 8:
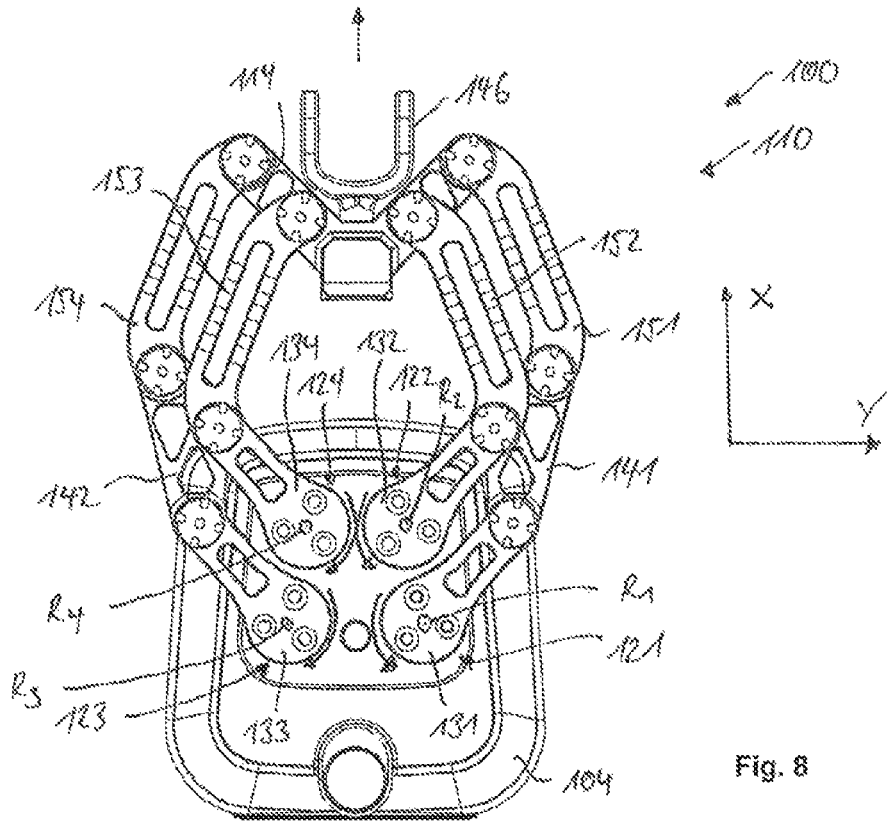
FIG. 8 the surgical manipulator device according to FIG. 4 in a fourth pose.

A second mounting point for the instrument receiving device 120 is formed by a sliding coupling 235 supported displaceably along the longitudinal axis L1 on an exterior of the sleeve 234, as indicated by the dashed lines of the sliding coupling 235' in FIG. 18. The sliding coupling 235 further comprises two opposite recesses 236 as described previously with reference to the foot housing 232. The sleeve 235 is connected to the first Cardan element 146 in a form-fit but rotatable manner by means of the recess 236 (cf. FIG. 2). The sliding coupling 235 serves for compensating for a changing distance between the first recesses 233 and the second recesses 236 when the first and second suspension arm arrangements 110, 112 are pivoted not in conformity to each other. It is conceivable, for example, that the first suspension arm arrangement 110 is pivoted into a position as shown in FIG. 6 and the second suspension arm arrangement 112 is pivoted into a position as shown in FIG. 7. In this case, the longitudinal axis L1 would not extend perpendicular to the motion planes B1, B2, but rather at an angle thereto. In this case, the distance between the recesses 236, 233 would be increased relative to the situation when the longitudinal axis L1 is perpendicular to the motion planes B1, B2. In order to compensate for said distance without introducing stresses or deformations to the first and second suspension arm arrangements 110, 112, the sliding coupling 235 is disposed for displacing.

The sliding coupling 235 preferably has as close a fit as possible to the sleeve 234 but without producing too much friction. To this end, the sliding coupling 235 can be provided with appropriate materials on the inner side thereof.

The linear drive 230 in the present embodiment comprises a spindle drive 238 disposed in the sleeve 234. The spindle drive 238 comprises a spindle 239 extending along the longitudinal axis L1 in the interior of the sleeve 234. At the top axial end 240 with respect to FIG. 19, the spindle 239 is received by means of a rotary bearing 241. At the bottom end 242 with respect to FIG. 19, the spindle 239 is coupled to an electric motor 243 rotatably driving the spindle 239 about the longitudinal axis L1. A corresponding control unit 245 for the electric motor 243 and an interface 246 for transmitting signals to the control unit 245 are disposed in an extension 244 of the foot housing 232.

A magnetic driver 250 is disposed on the spindle 239 and engages with the external thread of the spindle 239 by means of an internal thread 251. By rotating the spindle 239, the magnetic driver 250 can be displaced along the longitudinal axis L1. The magnetic driver 250 comprises a plurality of permanent magnets 252 at the radially outer side thereof. The linear drive 230 further comprises an output drive element 254 in the form of a bushing disposed in a sliding manner along the longitudinal axis at the outside of the sleeve 234. The output drive element 254 supports a further plurality of permanent magnets 255 on the inner side thereof, corresponding to the permanent magnets 252. In this manner, the output drive element 254 is coupled to the magnetic driver 250 and the output drive element 254 is thus displaceable back and forth along the longitudinal axis L1 by rotating the spindle 239. In this manner, the sleeve 234 can be fully closed in design and does not require any recesses or protrusions on the outside thereof, whereby the hygiene of the surgical manipulator device 100 of the present invention is substantially improved.

The drive element 254 further comprises a first coupling element 256, in this case implemented as a hook-shaped retaining finger. The first coupling element 256 is connected to the bushing body of the output drive element 254 by means of a screw connection 257. The first coupling element 256 is preferably made of an insulating plastic insulating a surgical instrument received by form-fit means 258 relative to the linear drive 230 and preferably relative to the bushing body of the output drive element 254.

For the case that the instrument receiving device 120 comprises a force/moment sensor unit 260, said unit is preferably mounted on the first coupling element 256. All forces acting on the surgical manipulator device 100 from a surgical instrument 102 are guided by means of the first coupling element 256. The force/moment sensor unit 260 can comprise a force/moment sensor, for example, disposed between the screw connection 257. It is further conceivable that individual force sensors, such as strain gauges, are disposed directly on a surface of the first coupling element 256. The force/moment sensor unit 260 is preferably connected to the control unit 245 and/or provides signals by means of the interface 246.

Figure 20:
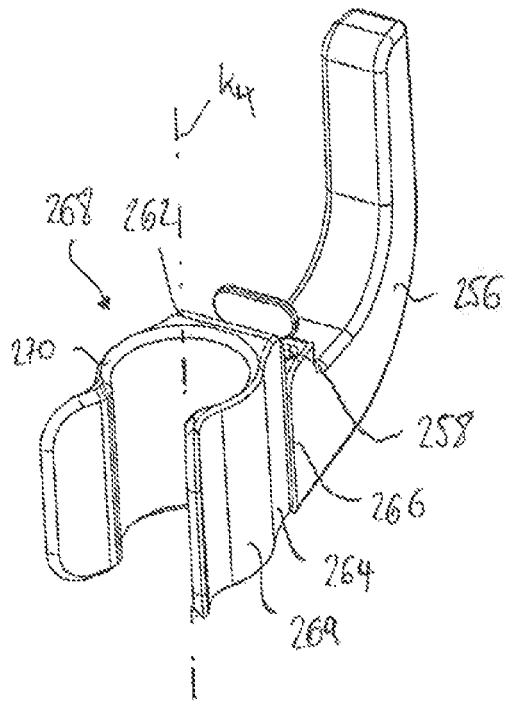
FIG. 20 a first view of a coupling element including an adapter.

The first coupling element 256 is shown again in FIG. 20 in a perspective view. As shown in FIG. 20, the first coupling element 256 supports a second coupling element 262 provided for clampingly receiving a surgical instrument.

The coupling element 262 comprises a main body 264 made of a flexible, electrically insulating material comprising form-fit means 266 for coupling to the form-fit means 258 of the instrument receiving device 120. Opposite the form-fit means 266, the base body 264 forms a clamping segment 268. The clamping segment 268 comprise a first and a second clamping jaw 269, 270 implemented mirror-symmetrically to each other. The clamping jaws 269 enclose a central axis K4 in a partially circular manner. The partially circular segment of the clamping jaws 269, 270 corresponds approximately to three-quarters of a circle. The clamping jaws 269, 270 each comprise a tab 272, 273 at the end of the circular segment 271 having the same axial length as the clamping jaws 269, 270. The tabs 272, 273 widen in that said tabs extend away from each other starting from the axis K4. Planes formed by the tabs 272, 273 preferably intersect at the central axis K4. The tabs 272, 273, by means of the beveling thereof, serve for easily introducing the instrument into the space between the clamping jaws 269, 270, and for easily removing the instrument 102 by manually grasping the tabs 272, 273 with the hands and pressing apart the clamping jaws 269, 270.

Figure 2:
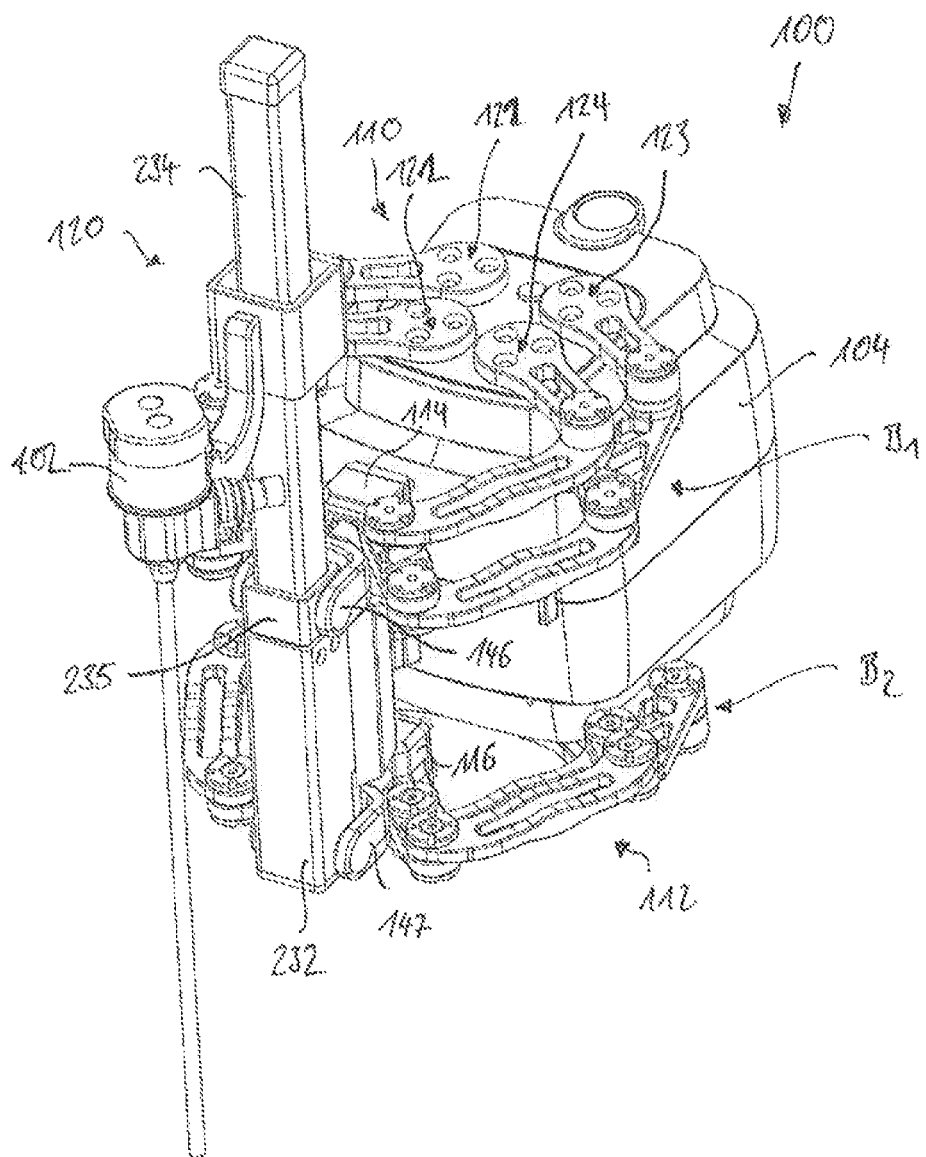
FIG. 2 a perspective view of the surgical manipulator device.

The clamping jaws 269, 270 provide form-fit fixing of the surgical instrument 102 in the directions perpendicular to the central axis K4, but also allow shifting of the surgical instrument 102 in the direction of the central axis K4, as can be seen in FIG. 2, for example.

In the region of the form-fit means 266, the coupling element 262 further comprises a clipping device 274 having a detent finger and a detent lug for engaging in a corresponding recess on the first coupling element 262. The grip 275 can be used for lifting the detent lug out of the corresponding detent groove on the first coupling element 256 and thus releasing the form-fit connection between the second coupling element 262 and the first coupling element 256. The form-fit means 266, 258 can be implemented as a dovetail guide or the like, for example.

In the schematic view (FIG. 22), the surgical manipulator device 100 is shown having further peripheral devices. The surgical manipulator device 100 in turn comprises the first and second suspension arm arrangements 110, 112 shown simplified in FIG. 22. In a first variant, the manipulator device 100 comprises a drive 210 and corresponding first, second, third, fourth motors 211, 212, 213, 214. In a second variant also shown in FIG. 22, the manipulator device 100 comprises a braking device 220 having corresponding first, second, third, and fourth brakes 221, 222, 223, 224. Because the schematic design is not different with respect to the drive 210 and the braking device 210, said components can be shown in other figures.

Figure 22:
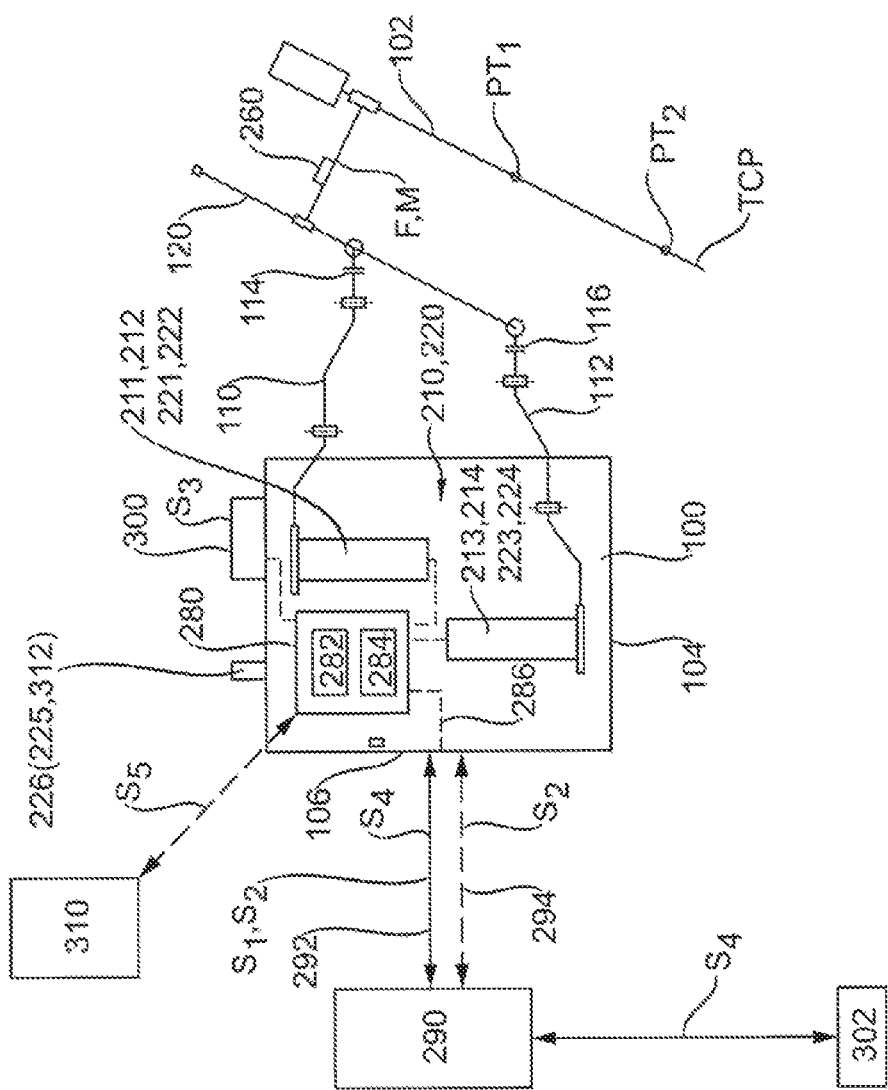
FIG. 22 a schematic view of the manipulator device having peripheral devices.

FIG. 22 is intended particularly for illustrating the electronic control unit 280. The electronic control unit 280 comprises a memory 282 and a processor 284 for controlling the displacement and positioning of the first and second mounts 114, 116. The electronic control unit 280 is connected to the interface 106 by means of a line 286 implemented as a mechatronic interface. By means of said interface 106, the surgical manipulator device is connected to an upper-level control unit 290. Said upper-level control unit 290 can be a surgical navigation system or the surgical mounting arm 1. The connection between the upper-level control unit 290 and the manipulator device 100 can be physical, by means of a line or a contact 292 to the electronic interface 106, or can be wireless by means of a wireless connection 394. For example, the upper-level control unit 290 and the manipulator device 100 can communicate by means of infrared radiation and the mechatronic interface 106 in this case is equipped with a corresponding receiver.

The control unit 280 of the manipulator device 100 can receive actuating signals 51 for the drive 210 and/or the braking device 220 directly from the upper-level control unit 290, for example. For the present embodiments, the control unit 280 does not require particular intelligence, but rather must merely provide corresponding actuating signals to the motors 211, 212, 213, 214 or the brakes 221, 222, 223, 224. It can also be provided, however, that positioning request signals S2 are provided by the upper-level control unit 290, that is, a position at which a tool center point or the tip of the surgical instrument 102, or a pivot point PT1, PT2 of the surgical instrument 102 should be. For this case, data is saved in the memory 282 representing the first and second suspension arm arrangements 110, 112 or the entire linkage or kinematic model in the upper-level coordinate system, for example the coordinate system of a navigation system, to the corresponding tool center point TCP or pivot point PT1, PT2.

Software means 282 are further saved in the memory 282 for performing the following steps when executed by the processor 284: determining a first vector and/or trajectory for a first mount 214, determining a second vector and/or a second trajectory for the second mount 216, providing actuating signals to the motors 111, 112, 113, 114 for displacing the first mount 14 in conformance with the first vector or the first trajectory and for displacing the second mount 16 in conformance with the second vector or second trajectory. A trajectory is typically preferably determined, as not only the destination is significant when displacing the instrument, but also the path from a current position to a target position must be considered. In this manner, it can occur that the surgical instrument 102 collides with parts of the patient's body, and for this reason a particular trajectory must be selected in order to avoid a collision.

For the case that a force/moment sensor unit 260 is provided, said unit is also connected to the control unit 280. The connection can be wired or wireless. The control unit 280 preferably comprises corresponding software means in the memory 282 thereof set up for processing signals provided by the force/moment sensor unit 260 and for controlling the drive 210 and/or a linear drive of the instrument receiving device 120 or optionally the braking device 220 accordingly. The force acting on the instrument receiving device 120 from the instrument 102 can represent a user's command. It is possible, for example, that a surgeon grasps the surgical instrument 102 manually and wishes to guide the same to a particular point. In this case, forces F and moments M act on the instrument receiving device 120 from the instrument 102 and are then captured by means of the force/moment sensor unit. Corresponding signals are then provided to the control unit 280. The software means are preferably implemented, when executed on the processor 284, for causing the control unit 280 to determine displacements or a trajectory or vector for the first and second suspension arm arrangements 110, 112 and/or for a linear drive 238 of the instrument receiving device 120, in order to compensate for the forces F and moments M acting on the instrument receiving device 120 and to provide control signals to the drive 210, the linear drive 238, and/or the braking device 220 conforming to said displacement, trajectory, or vector, in order to perform the displacement according to the trajectory or the vector. That is, the surgical manipulator 100 responds to the user's command and attempts to assume a pose for compensating for the forces F and moments M acting on the instrument receiving device 120.

Because such a procedure is not desired at all times, it is preferable that the surgical manipulator 100 comprises an integrated input system 300. The integrate input system 300 can comprise a microphone, for example, and/or a touch display for placing the surgical manipulator device 100 in said mode wherein the described software is executed. It can be provided, for example, that the user must enter a command "manual guide mode" or "follow mode" and said spoken command is captured by means of the microphone and corresponding signals are provided to the control unit 280. Corresponding speech recognition software means provide actuating signals, so that the software means are executed on the processor 284.

Alternatively or in addition, a foot pedal 302 can also be provided and in the present embodiment example is coupled to the upper-level control unit 290. By means of the foot pedal 302, a corresponding signal S4 can be provided to the upper-level control unit 290, so that the upper-level control unit 290 forwards the corresponding signal S4 and provides the same to the control unit 280 of the manipulator device 100.

In a further embodiment, it can be provided that the surgical manipulator device 100 communicates with a handheld mobile device 310. The mobile device 310 can be a tablet PC, a mobile phone, or another device implemented in the manner of a remote control, for example. Signals S5 can be transmitted wirelessly from the mobile device 310 to the control unit 280 comprising a corresponding receiver to this end. The mobile device 310 can also be implemented for displaying a representation of the pose of the manipulator device 100, for example a simplified graphic image of the pose. It can be provided that software is executed on said mobile device for positioning the surgical instrument by means of drag & drop, particularly by means of a touch display. If the patient is also depicted having particular landmarks on the mobile device, then the surgical instrument can be positioned in an automated manner by means of the mobile device 310 by selecting a particular landmark. The processing of the positioning request signals sent to the control unit 280 correspondingly as the signal S5, occurs in the manner described above.

In a similar manner, the integrated input system 300 can also comprise a display on which such representations are displayed.

It is also possible, of course, to output warning signals by means of the integrated input system 300 or the mobile device 301 if, for example, a predefined working space of the surgical manipulator device 100 is departed, for example if a user manually positions the surgical instrument 102 in the manual positioning mode, as described above, and it is thereby determined that said instrument is guided outside of a predefined working space.

A pushbutton 226 is disposed on the housing 104. The pushbutton 226 has been described above with reference to the braking device 220. The pushbutton can be assigned depending on the design of the surgical manipulator device, that is, whether a drive 210 or a braking device 220 is provided. If the braking device 220 is provided, then the pushbutton 226 is preferably parameterized as a releasing device 225 and the brakes 221, 222, 223, 224 can be released by means of the pushbutton 226.

For the case that a drive 210 having motors 211, 212, 213, 214, is provided, the pushbutton is preferably parameterized as what is known as a home button 312. In the present embodiment, if the pushbutton is parameterized as a home button 312, pressing the pushbutton causes the surgical manipulator device to travel to an initial, predefined pose saved in the memory 282. In this manner, it is possible to travel to a predetermined and presaved pose simply by pressing the pushbutton 226. It is preferably further provided that the presaved pose can be saved by means of the pushbutton 226. To this end, the pushbutton 226 is pressed and held for a predetermined duration (for example, 3 seconds) and the current pose is saved as a presaved pose in the memory 282 in order to be called up and traveled to when the pushbutton 226 is pressed again.

Figure 21:
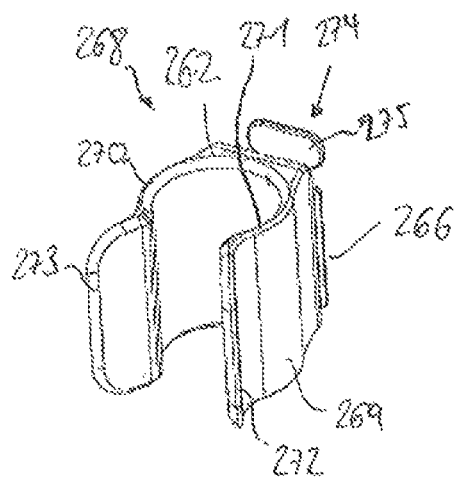
FIG. 21 a second view of the coupling element from FIG. 20.
Figure 23:
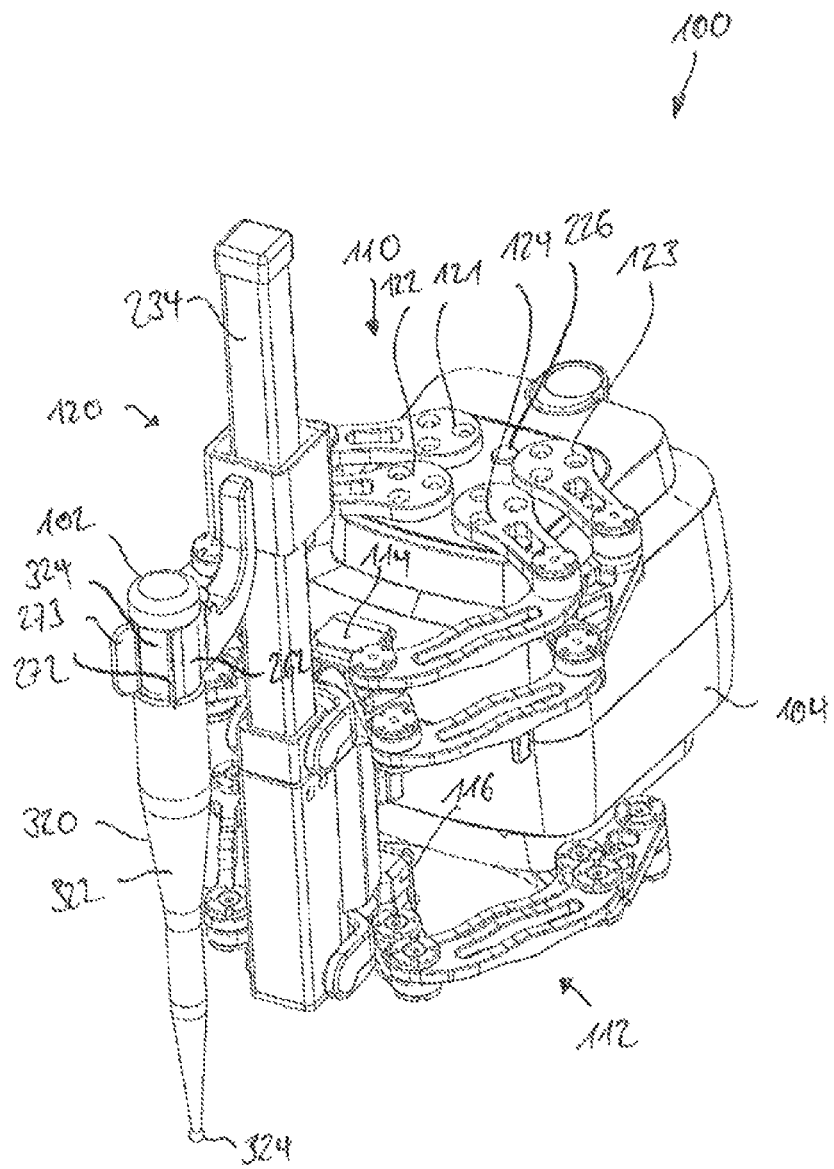
FIG. 23 a perspective view of the surgical manipulator device having a pivot point gage received.

In order to initially read in or define a pivot point for a surgical instrument 102, a pivot point gage 320 can be received at the first and second mounts 114, 116 as a surgical instrument 102 according to the present invention. This is shown in FIG. 23. The pivot point gage 320 is more precisely received at the instrument receiving device 120 by means of the second coupling element 262 describe in detail with reference to FIG. 21.

The pivot point gage 320 comprises a shaft 322 and a narrow region 324. The narrow region is implemented for being received between the clamping jaws 270, 269. The axial extent of the narrow segment 224 corresponds to the axial length of the clamping jaws 269, 270 with respect to the axis K4. That is, the pivot point gage 320 has a defined position relative to the coupling element 262 and thus also relative to a coordinate system of the surgical manipulator device 100. The axial length of the pivot point gage 320 is known and thus also the position of the probe head 324 implemented at an axial end of the pivot point gage 320. For reading in a pivot point PT, the user guides the manipulator device 100 manually, or electrically controlled, to a pose in which the probe head 324 is disposed at the patient-specific pivot point of the patient.

The control unit 280 preferably comprises software means for this case for calculating, when executed on the processor 284, the setting of the individual joints and the pose of the first and second suspension arm arrangements 110, 112, and the position and setting of the instrument receiving device 120, coordinates of the probe head 324, and thus also of the pivot point PT. For saving said pivot point coordinates and/or for providing the pivot point coordinates to the interface 106, a user preferably actuates a user input, for example pressing the pushbutton 226 parameterized for this purpose. It can also be provided that a pushbutton or the like is provided on the pivot point gage 320 for saving and/or providing the coordinates.

The control unit 280 is preferably further set up for calculating the pivot point with respect to the surgical instrument and displacing correspondingly along the longitudinal axis K4 when a different surgical instrument 102 is received, having a different axial length from the shaft 322 of the pivot point gage 320. If, for example, an endoscope is received (cf. FIG. 2), then the axially lower tip of the endoscope can be positioned deviating from the probe head 324. If the geometry of the endoscope is known, then the position of the pivot point can be transformed accordingly.

Figure 24:
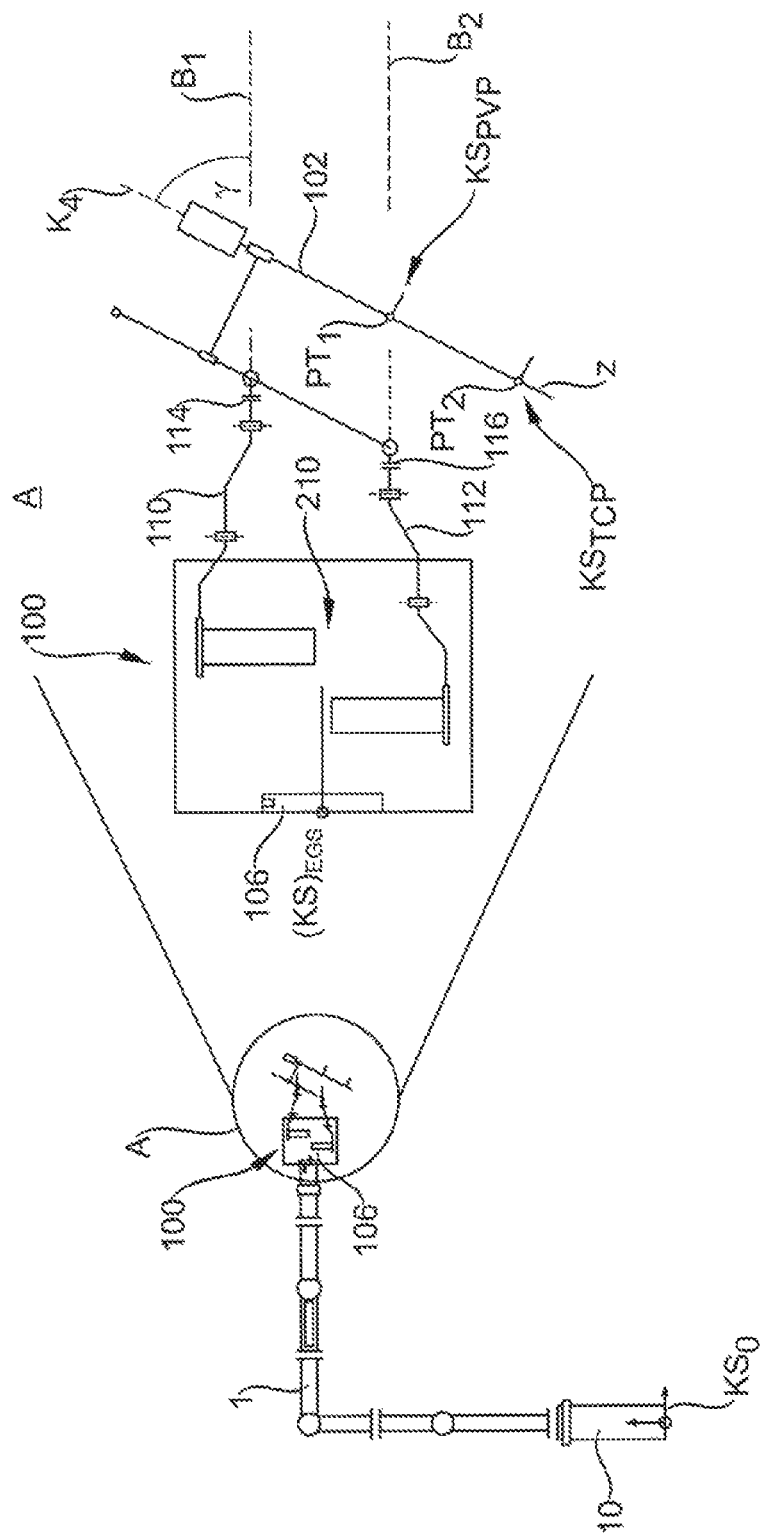
FIG. 24 a schematic view of the pivot point control system.

FIG. 24 again illustrates the determining of the pivot point PT and the corresponding calculation. The surgical manipulator device 100 is again shown schematically in FIG. 24, while detail A of the left side of FIG. 24 is again shown magnified on the right side. The surgical manipulator device 100 in the present embodiment example is received in a mounting arm 1 as has already been fundamentally described with reference to FIG. 1. The schematic view of the manipulator device 100 is identical to the schematic view of the manipulator device 100 from FIG. 24 and in this respect reference is made in full to the above description. Identical and similar elements also have identical reference numerals.

The mounting arm 1 is initially fixedly mounted on an operating table and has a coordinate system KS0 as a base coordinate system. The patient is also present in the coordinate system KS0, as the position of the patient is typically not displaced relative to the base 10 of the mount arm 1 during an operation.

The described pivot point gage 320 can be sued for determining a tool center point coordinate system $KS_{TCP}$ at the first pivot point PT1. The pivot point PT1 is the pivot point defined by means of the pivot point gage 320 using the probe head 324. The Z-axis of the coordinate system $KS_{TCP}$ is aligned in the direction of the axis K4 defined by the instrument receiving device 120. The orientation of the axis K4 is parallel to the axis L1 of the linear drive and can run at an angle (as shown in FIG. 22) to the first and second motion planes B1, B2. The setting angle γ between the axis K4 and the first motion plane B1 is defined by differentially actuating the first and second suspension arm arrangements 110, 112.

If a different surgical instrument 112 is received, the pivot point PT1 is initially located at the point read in using the pivot point gage 320. The pivot point PT1 can, however, also be shifted along the longitudinal axis K4 by calculating. For example, the current pivot point shifts from pivot point PT1 to pivot point PT2 when the surgical instrument 102 is introduced into the body of a patient. The endoscope, for example, to be progressively guided along as the operation progresses in order to reproduce the operating area, can be displaced for what is known as a keyhole operation such that the pivot point is always located approximately in the region of the keyhole. In some cases, the pivot point can also be located outside of the axis K4.

A transformation matrix is also preferably determined between the base 10, that is, the base coordinate system KS0, and one of the coordinate systems at the pivot point $KS_{PVP}$ or the initial pivot point $KS_{TCP}$. Said transformation matrix is preferably provided by means of the interface 106 and/or saved in the memory 282.

The definition of the pivot point PT1, PT2 and the saving thereof can also be used for cyclically pivoting the surgical instrument 102. Such cyclical pivoting is used by users, for example, for obtaining a spatial impression of the field observed by the endoscope. For the case that an endoscope is received as the surgical instrument 102, the following method is preferred and is explained in more detail with reference to FIG. 25: (1.) The user positions the endoscope; (2.) The user starts pivoting motions or the control unit 280 starts automatically after positioning; (3.) Support points 330a, 330b, 330c, 330d relative to the current pose are determined for an endoscope tip 103, wherein the support points 330a, 330b, 330c, 330d together define a path 332. The path 332 can thereby be planned, that is, can run continuously through the support points 330a, 330b, 330c, 330d. Alternatively, the support points 330a, 330b, 330c, 330d are traveled to directly and discretely. The path 332 is preferably elliptical. The elliptical path 332 is preferably determined by the control unit 280 using the support points 330a, 330b, 330c, 330d. The instrument 102 is then pivoted on the path 332. A pivot approach path 334 is required for this purpose. The instrument 102 is then preferably displaced such that the tip 103 travels along the path 332 until a corresponding interrupt signal is received at the control unit 280 or is generated by the same. A pivot departure path 336 is then provided for pivoting out back the initial position.

Figure 25:
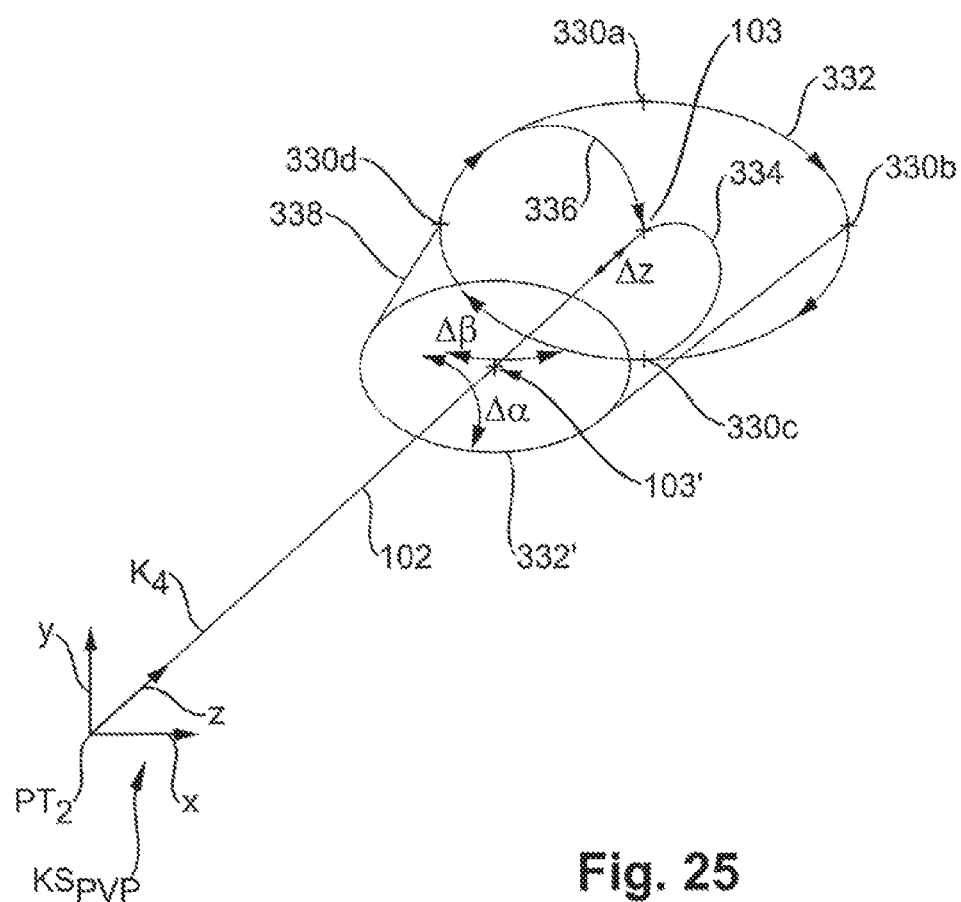
FIG. 25 a schematic view of a rotation of the surgical instrument about the pivot point.
Figure 26:
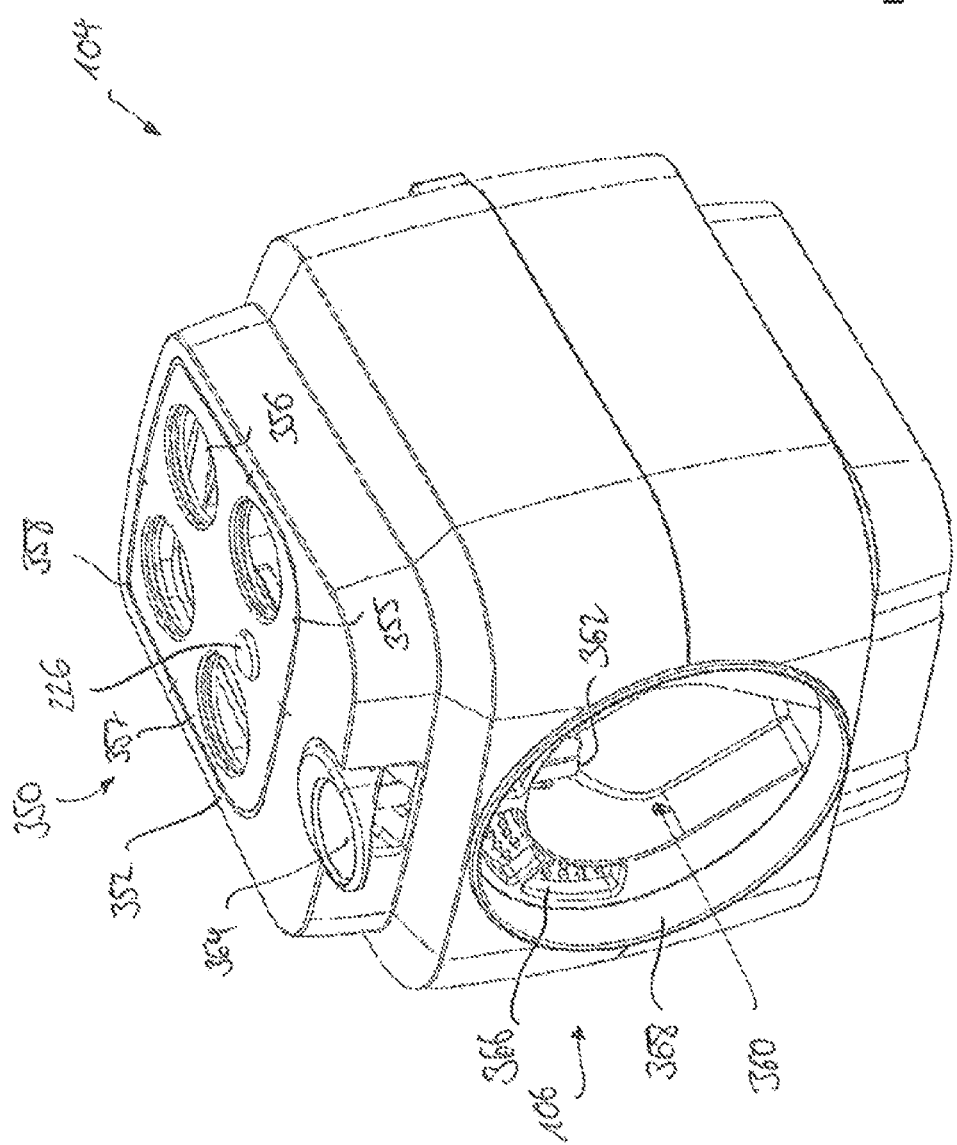
FIG. 26 a perspective view of a housing of the surgical manipulator device having an indicator device.

If the instrument 102 is shifted along the longitudinal axis K4 thereof in the Z-direction relative to the pivot point coordinate system $KS_{PVP}$, the tip 103 comes to a point labeled as 103' in FIG. 25, for example. The instrument 102 is thus shifted by a distance ΔZ. For this case, the path 332 is transformed to the path 332' located on the enclosing sphere 338 defined between the pivot point PT2 and the path 332. The transformed path 332 is preferably determined by the control unit 280 using suitable software means.

The surgical manipulator device 100 further preferably comprises an indicator device 350 for indicating one or more statuses of the surgical manipulator device 100. The general function of such an indicator device is also described in EP 3 130 305 A1 with reference to joints of the mounting arm disclosed and claimed therein, and the teaching thereof can be used analogously for the present manipulator device, particularly the joints thereof.

The indicator device 350 can fundamentally be implemented arbitrarily, for example comprising a display, or in the embodiment example shown in the figures, the indicator device comprises a plurality of indicator segments, namely initially a top indicator segment 352 (FIG. 23) and a bottom indicator segment (FIG. 5). The terms "top" and "bottom" in the present embodiment example relate to an initial setting of the surgical manipulator device 100, wherein the first and second motion planes B1, B2 are oriented substantially horizontally and the top indicator segment 352 faces upward.

The top and bottom indicator segments 352, 354 are implemented as annular light strips, and particularly as a plurality of LED elements. The two indicator segments 352, 354 are identical and mirror-symmetrical in design with respect to the first and second motion planes B1, B2. This has the advantage that for every orientation of the surgical manipulator device 100, a user can see either the top indicator segment 352 or the bottom indicator segment 354.

In addition, according to the present embodiment example, each of the top and bottom indicator segments 352, 354 has four individual segments 355, 356, 357, 358. The first indicator segment 355 is thereby associated with the first lever pivot point 121, the second indicator segment 356 is associated with the second lever pivot point 122, the third indicator segment 357 is associated with the third lever pivot point 123, and the fourth indicator segment 358 is associated with the fourth lever pivot point 124. It is provided, for example, that when one of the lever pivot points 121, 122, 123, 124 or the corresponding lever 131, 132, 133, 134 is displaced, the correspondingly associated segment 355, 356, 357, 358 lights up to indicate the actuation. Because two each of the levers are connected together and cannot be displaced independently of each other, it can also be provided that the first segment 355 is associated with the first motor, the fourth indicator segment 352 is associated with the second motor, the second indicator segment 356 is associated with the third motor, and the third indicator segment 358 is associated with the fourth motor when a drive 210 is provided for the manipulator device 100. In this manner, spatial association of the four indicator segments 355, 356, 357, 358 with the corresponding actuated motors 211, 212, 213, 214 is provided. In this manner, the user can see which of the motors 211, 212, 213, 214 is actuated and in which direction the instrument or the first and second mounts 114,1 16 and the surgical instrument 102 received thereon will be displaced.

It can also be provided that a point of light runs along the path of the annular top or bottom indicator segments for assistance purposes in order to indicate a direction of motion of a lever 131 through 139. This is particularly preferable if the manipulator device 100 is implemented as a passive manipulator device 100 and comprise a braking device 220. When the brakes 221, 222, 223, 224 are released, the point of light displacing around or along an indicator segment 355, 356, 357, 358 can be used in this manner for indicating a direction in which a user must displace the surgical instrument 102 in order to bring the same to a pivot point, for example, or to another predetermined pose.

Further options for indicating have been described above. Indicating is understood particularly in this sense to be placing the segments 352, 354 partially or completely in an illuminated state from a non-illuminated state; changing a color, changing an intensity, changing a flashing frequency or intensity variance frequency, indicating one or more partially circulating points of light by means of a higher or lower intensity or a different color.

In a further embodiment, it can also be provided that the indicator device 350 comprises one or more infrared light sources by means of which the indicator device 350 can communicate with a surgical navigation system. The infrared light is preferably connected with the remainder of the LEDs and thus indicates the same state as the indicator device 350 overall. This means that the infrared light can be used to inform a surgical navigation system that a motor has been activated, for example, or another state of the manipulator device 100 has been changed.

It can also be provided that said infrared light is used for wirelessly transmitting other data, particularly pivot point coordinates or the like, to the surgical navigation system.

Even though it is shown in the present embodiment example (FIG. 25) that the segments 355, 356, 357, 358 together form a ring, in other embodiment examples it can also be provided that each of said segments 355, 356, 357, 358 is intrinsically annular and associate with a lever pivot point 121 through 129. It can also be provided that the ring of the top and bottom indicator segments 352, 354 is not closed, or has a different geometry. It is also conceivable to provide further indicator devices or alternative indicator devices on the sides of the housing 104.

FIG. 25 further shows the interface 106. Said interface comprise a recess 360 at the center thereof having a plurality of flanks for coupling to a protrusion of a stand, mounting arm, or the like in a form-fit manner. A stud 362 is provided for locking the form-fit connection and engages in a corresponding recess on the protrusion of the mounting arm or stand, thus locking the form-fit connection. Said stud can be displaced upward with reference to 25 by pressing a pushbutton 364. The pushbutton 365 is pretensioned in the locked position by means of a spring (cf. FIG. 16, 17).

The interface 106 further comprises a plurality of electrical contacts reference in the present embodiment example overall as 366. A collar 368 protrudes axially somewhat all around the interface 106, and serves particularly for sealing off the interface relative to the surrounding area. The electrical contacts 366 are thus prevented from making contact with liquids or the like.

The invention claimed is:

1. A surgical manipulator device for positioning a surgical instrument, the surgical manipulator device comprising:
   a frame;
   a first mount and a second mount configured to mount the surgical instrument;
   a first suspension arm arrangement supported on the frame and configured to connect the frame to the first mount in an articulated manner; and
   a second suspension arm arrangement supported on the frame and configured to connect the frame to the second mount in an articulated manner,
   wherein the first and the second suspension arm arrangements are spaced apart and each displaceable relative to the frame in first and second motion planes parallel to each other, so that the first mount is displaceable in the first motion plane and the second mount is displaceable in the second motion plane,
   wherein the first suspension arm arrangement is coupled to the frame at four first lever pivot points of the first suspension arm arrangement and the second suspension arm arrangement is coupled to the frame at four second lever pivot points of the second suspension arm arrangement, and
   wherein the four first lever pivot points of the first suspension arm arrangement and the four second lever pivot points of the second suspension arm arrangement are disposed in a V shape, disposed on four common axes of rotation, or offset parallel to each other.

2. The surgical manipulator device according to claim 1, wherein the first suspension arm arrangement comprises:
   a first lever, a second lever, a third lever, and a fourth lever, each rotatably supported on respective first lever pivot points of the first suspension arm arrangement on the frame;
   a first suspension arm rotatably coupled to the first and second levers and a second suspension arm rotatably coupled to the third and fourth levers; and
   first and second bars rotatably coupled to the first suspension arm on one side and rotatably coupled to the first mount on the other side, and third and fourth bars rotatably coupled to the second suspension arm on one side and rotatably coupled to the first mount on the other side.

3. The surgical manipulator device according to claim 1, wherein the second suspension arm arrangement comprises:
   a fifth lever, a sixth lever, a seventh lever, and an eighth lever, each rotatably supported on respective second lever pivot points of the second suspension arm arrangement on the frame;
   a third suspension arm rotatably coupled to the fifth and sixth levers and a fourth suspension arm rotatably coupled to the seventh and eighth levers; and
   fifth and sixth bars rotatably coupled to the third suspension arm on one side and rotatably coupled to the second mount on the other side, and seventh and eighth bars rotatably coupled to the fourth suspension arm on one side and rotatably coupled to the second mount on the other side.

4. The surgical manipulator device according to claim 1, wherein:
   the first suspension arm arrangement comprises a first parallelogram, a second parallelogram, a third parallelogram, and a fourth parallelogram; and
   the second suspension arm arrangement comprises a fifth parallelogram, a sixth parallelogram, a seventh parallelogram, and an eighth parallelogram.

5. The surgical manipulator device according to claim 4, wherein the first and second parallelograms comprise a first common pivot point, and the third and fourth parallelograms comprise a second common pivot point.

6. The surgical manipulator device according to claim 1, further comprising a drive comprising a first motor and a second motor for the first suspension arm arrangement and a third motor and a fourth motor for the second suspension arm arrangement.

7. The surgical manipulator device according to claim 6, wherein the first and second motors drive a lever disposed distal to the first mount, and the third and fourth motors drive the lever disposed proximal to the second mount.

8. The surgical manipulator device according to claim 1, further comprising a braking device configured to actively brake the first and second suspension arm arrangements, and a releasing unit configured to selectively release one or more degrees of freedom of the first and/or second suspension arm arrangement.

9. The surgical manipulator device according to claim 8, wherein the braking device comprises a first brake and a second brake for the first suspension arm arrangement, and a third brake and a fourth brake for the second suspension arm arrangement.

10. The surgical manipulator device according to claim 9, wherein the first and second brakes are configured to brake a lever disposed distal to the first mount, and the third and fourth brakes are configured to brake the lever disposed proximal to the second mount.

11. The surgical manipulator device according to claim 1, further comprising an instrument receiving device coupled to the first and the second mounts.

12. The surgical manipulator device according to claim 11, wherein the instrument receiving device comprises a force/moment sensor unit configured to sense forces and moments acting on the instrument receiving device from the surgical instrument received at the instrument receiving device.

13. The surgical manipulator device according to claim 11, wherein the instrument receiving device comprises form-fit means configured to receive a coupling element for the surgical instrument.

14. The surgical manipulator device according to claim 13, wherein the instrument receiving device comprises a linear drive configured to position the surgical instrument at least partially perpendicular to the first and second motion planes.

15. The surgical manipulator device according to claim 14, wherein the linear drive comprises an elongated sleeve, a spindle drive disposed in the sleeve, and an output drive element supporting the form-fit means,
   wherein the spindle drive drives a magnetic driver disposed in the sleeve, and
   wherein the output drive element is supported externally and linearly displaceably on the sleeve and is coupled to the magnetic driver via magnetic force.

16. The surgical manipulator device according to claim 14, wherein the instrument receiving device comprises a rotary drive provided for rotating a received surgical instrument about an axis of rotation parallel to a drive direction of the linear drive.

17. The surgical manipulator device according to claim 1, further comprising an electronic control unit comprising a storage and a processor configured to control motion and to position at least the first and second mounts.

18. The surgical manipulator device according to claim 1, further comprising an indicator device configured to indicate one or more statuses of the surgical manipulator device.

19. The surgical manipulator device according to claim 18, wherein the indicator device is configured to indicate motion of at least one part of the first and second suspension arm arrangements.

20. A method for positioning a surgical instrument via a surgical manipulator device,
the surgical manipulator device comprising:
 a frame;
 a first mount and a second mount configured to mount the surgical instrument;
 a first suspension arm arrangement supported on the frame and configured to connect the frame to the first mount in an articulated manner; and
 a second suspension arm arrangement supported on the frame and configured to connect the frame to the second mount in an articulated manner,
 wherein the first and the second suspension arm arrangements are spaced apart and each displaceable relative to the frame in first and second motion planes parallel to each other, so that the first mount is displaceable in the first motion plane and the second mount is displaceable in the second motion plane, and
 wherein the first suspension arm arrangement is coupled to the frame at four first lever pivot points of the first suspension arm arrangement and the second suspension arm arrangement is coupled to the frame at four second lever pivot points of the second suspension arm arrangement; and
the method comprising:
 determining a first vector and/or trajectory for the first mount for mounting the surgical instrument and lying within the first motion plane;
 determining a second vector and/or trajectory for the second mount for mounting the surgical instrument and lying within the second motion plane;
 displacing the first mount in correspondence with the first vector or the first trajectory via the first suspension arm arrangement supported on the frame and connecting the frame to the first mount; and
 displacing the second mount in correspondence with the second vector or the second trajectory via the second suspension arm arrangement connecting the frame to the second mount,
 wherein the first and second motion planes are parallel to each other.

21. The method according to claim 20, further comprising:
 determining a first rotation for the first mount;
 determining a second rotation for the second mount;
 rotating the first mount in correspondence with the first rotation via the first suspension arm arrangement supported on the frame; and
 rotating the second mount in correspondence with the second rotation via the second suspension arm arrangement supported on the frame,
 wherein the axes of rotation of the rotations are disposed perpendicular to the first and second motion planes.

22. The method according to claim 20, further comprising:
 receiving a first surgical instrument at the first and second mounts; and
 capturing a pivot point of the first surgical instrument relative to an object by traveling to the pivot point via the first and second mount.

23. The method according to claim 22, further comprising:
 receiving a signal representing an approach request of the pivot point; and
 determining the first and second vector or the first and second trajectory, such that a received surgical instrument is positioned at the pivot point.

24. The method according to claim 20, wherein the surgical instrument is a probe instrument, the method further comprising:
 traveling to a first anatomical landmark of a patient via the probe instrument;
 saving first landmark data representing the pose of the first and second suspension arm arrangements and/or the position of the first and second mounts; and
 linking the first landmark data to first image data representing at least one prerecorded tomograph of the patient.

25. A coupling element for a surgical manipulator device, the surgical manipulator device comprising:
 a frame;
 a first mount and a second mount configured to mount a surgical instrument;
 a first suspension arm arrangement supported on the frame and configured to connect the frame to the first mount in an articulated manner;
 a second suspension arm arrangement supported on the frame and configured to connect the frame to the second mount in an articulated manner; and
 an instrument receiving device coupled to the first and the second mounts, wherein the instrument receiving device comprises first form-fit means configured to receive the coupling element,
 wherein the first and the second suspension arm arrangements are spaced apart and each displaceable relative to the frame in first and second motion planes parallel to each other, so that the first mount is displaceable in the first motion plane and the second mount is displaceable in the second motion plane, and
 wherein the first suspension arm arrangement is coupled to the frame at four first lever pivot points of the first suspension arm arrangement and the second suspension arm arrangement is coupled to the frame at four second lever pivot points of the second suspension arm arrangement; and
the coupling element comprising:
 a main body made of a flexible, electrically insulating material,
 wherein the main body comprises second form-fit means for coupling to the instrument receiving device, and a clamping segment for clampingly coupling to the surgical instrument, such that the coupling element couples the surgical instrument to the instrument receiving device.

26. An instrument receiving device for a surgical manipulator device, the instrument receiving device configured to receive a surgical instrument, the surgical manipulator device comprising:
- a frame;
- a first mount and a second mount configured to mount the surgical instrument;
- a first suspension arm arrangement supported on the frame and configured to connect the frame to the first mount in an articulated manner; and
- a second suspension arm arrangement supported on the frame and configured to connect the frame to the second mount in an articulated manner,
- wherein the first and the second suspension arm arrangements are spaced apart and each displaceable relative to the frame in first and second motion planes parallel to each other, so that the first mount is displaceable in the first motion plane and the second mount is displaceable in the second motion plane, and
- wherein the first suspension arm arrangement is coupled to the frame at four first lever pivot points of the first suspension arm arrangement and the second suspension arm arrangement is coupled to the frame at four second lever pivot points of the second suspension arm arrangement; and the instrument receiving device comprising:
- a linear drive for positioning the surgical instrument, wherein the linear drive comprises an elongated sleeve, a spindle drive disposed in the sleeve, and an output drive element for coupling to the surgical instrument,
- wherein the spindle drive drives a magnetic driver disposed in the sleeve and the output drive element is supported externally and linearly displaceably on the sleeve and is coupled to the magnetic driver via magnetic force.

* * * * *